(12) United States Patent
Kiyama et al.

(10) Patent No.: US 10,184,100 B2
(45) Date of Patent: Jan. 22, 2019

(54) LIQUID DELIVERY DEVICE AND CELL CULTURE DEVICE USING SAME

(71) Applicant: Hitachi, Ltd., Tokyo (JP)

(72) Inventors: Masaharu Kiyama, Tokyo (JP); Guangbin Zhou, Tokyo (JP); Takayuki Nozaki, Tokyo (JP); Shizu Matsuoka, Tokyo (JP); Masakazu Sugaya, Tokyo (JP); Taku Nakamura, Tokyo (JP); Koichi Terada, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 426 days.

(21) Appl. No.: 14/894,033

(22) PCT Filed: Aug. 23, 2013

(86) PCT No.: PCT/JP2013/072597
§ 371 (c)(1),
(2) Date: Nov. 25, 2015

(87) PCT Pub. No.: WO2015/025425
PCT Pub. Date: Feb. 26, 2015

(65) Prior Publication Data
US 2016/0108350 A1    Apr. 21, 2016

(51) Int. Cl.
*C12M 3/00* (2006.01)
*C12M 1/34* (2006.01)
*C12M 1/00* (2006.01)
*C12M 1/26* (2006.01)

(52) U.S. Cl.
CPC ............ *C12M 21/08* (2013.01); *C12M 29/00* (2013.01); *C12M 33/00* (2013.01); *C12M 41/30* (2013.01); *C12M 41/34* (2013.01); *C12M 41/44* (2013.01)

(58) Field of Classification Search
CPC ...... C12M 21/08; C12M 29/00; C12M 33/00; C12M 41/30; C12M 41/34; C12M 41/44
See application file for complete search history.

(56) References Cited

U.S. PATENT DOCUMENTS 6,165,270 A * 12/2000 Konishi et al. ......... B05C 11/08
118/313

FOREIGN PATENT DOCUMENTS

| JP | 62-185166 A | 8/1987 |
| JP | 2000-201667 A | 7/2000 |
| JP | 2006-149268 A | 6/2006 |
| JP | 2006-314250 A | 11/2006 |

(Continued)

OTHER PUBLICATIONS

International Search Report of PCT/JP2013/072597.

*Primary Examiner* — Gautam Prakash
(74) *Attorney, Agent, or Firm* — Mattingly & Malur, PC

(57) ABSTRACT

The liquid feeder includes a liquid feeding pipe having a liquid introduce port and a liquid discharge port, a housing container which holds liquid to be introduced from the liquid introduce port, a liquid feed mechanism which feeds the liquid in the liquid feeding pipe to the liquid discharge port, a gas introduce unit which introduces gas into the liquid feeding pipe, and a liquid level detection unit which detects an advancing liquid level of the liquid to be fed in the liquid feeding pipe. The gas introduce unit is connected to a branch part provided in the liquid feeding pipe on the upstream side of the liquid feed mechanism. The liquid level detection unit is provided on the downstream side of the branch part.

12 Claims, 10 Drawing Sheets

(56) References Cited

FOREIGN PATENT DOCUMENTS

| | | |
|---|---|---|
| JP | 2007-222120 A | 9/2007 |
| JP | 2008-271862 A | 11/2008 |
| WO | 2007/083465 A1 | 7/2007 |

\* cited by examiner

LIQUID DELIVERY DEVICE AND CELL CULTURE DEVICE USING SAME

TECHNICAL FIELD

The present invention relates to a liquid delivery device (or a liquid feeder) and a cell culture device (or a cell culture apparatus) for culturing cells by using the liquid feeder.

BACKGROUND ART

In regenerative medicine for treating the disease by using own cells or cells of other person, the cells collected from a living body are used for transplantation treatment by increasing the number of cells by culturing them or constructing a tissue in a certain form. The culture of the cells used for the treatment should be performed as complying with the good manufacturing practice (GMP) in a clean room for the cell culture called as a cell processing center (CPC). The problem here is a point that it is necessary to use much labor and cost relative to cell preparation for one patient since the cells are cultured by a manual operation performed by a technical expert. In addition, there is a biological contamination risk caused by the manual operation.

As a method to solve the problems, an apparatus in which a cell culture process is automatically performed in a closed system has been developed. By using a closed-system culture container which does not need an operation for opening/closing a lid of the culture container, the cell culture process can be automated, and the biological contamination risk can be reduced.

A major operation which is manually operated at the time of the culture includes a cell seeding operation for feeding liquid culture medium in which the cells are suspended to a culture dish and an operation for exchanging the liquid culture medium which is regularly performed when the cells are cultured. In the manual operation, a predetermined amount of liquid is collected by using a dispenser used by attaching a disposable dispensing tip or a measuring pipette, and the liquid is added from the liquid culture medium in the liquid bottle to the culture dish. That is, the dispensation includes two actions, i.e., to determine the amount of the liquid and collect the liquid and to transfer the liquid to a target position. Regarding the automatic culture apparatus, there is a method for mechanizing the similar dispenser and adding the liquid by interlocking the collecting and transferring operations similarly to the manual operation. Since it is necessary to place the whole apparatus in a sterile environment, the automatic culture apparatus increases in size. On the other hand, when the pump is used for the dispensation operation, there is a method for connecting a space between the liquid bottle and the culture dish with a disposable tube and determining the liquid amount and feeding the liquid by the pump at the same time. In this case, it is preferable that inside the tube in which the liquid is fed be maintained in a sterile state, and an automatic apparatus can be reduced in size. PTL discloses an automatic culture apparatus for using a mechanized dispenser, and PTL 2 discloses an apparatus for feeding the liquid by the pump.

CITATION LIST

Patent Literatures

PTL 1: JP 2006-149268 A
PTL 2: JP 2007-222120 A

SUMMARY OF INVENTION

Technical Problem

When the pump is used for the dispensation in PTL 2, the culture medium or the cell suspension pass through the tube, and the liquid is confined in the tube when the pump is stopped. When this state continues, the culture medium dries in the tube, and the tube is clogged. Therefore, as a measure, a method for immediately moving the liquid such as chemicals in the tube by introducing air into the tube is disclosed. However, a space to a middle of the tube connected to a container for holding the culture medium is filled with the culture medium, and the culture medium stays there, and there is no description on discharge of the culture medium.

Regarding a liquid feeding method by using the pump, a liquid feeding method and a liquid feeder can be considered in which the liquid culture medium is not maintained in the pipeline connected to a target container. A liquid feeder 1 for using a drop of the liquid is illustrated in FIG. 3. A liquid bottle 2 holds the liquid and can airtightly hold the liquid therein with a lid. A pipeline 3 is provided in one of lids and adjusts air pressure. A filter 4 is provided at an opening end and has a mesh size of 0.22 μm. The filter 4 is opened to outside air. A supply pipe 5 is provided in the lid and has an opening end in the liquid bottle 2 which has contact with the liquid and becomes a liquid discharge port. One end of a pump 6 is connected to the supply pipe 5, and another end is connected to a discharge pipe 7. A receptor 8 is a target of feeding the liquid. A branch point 9 is provided above the liquid level in the liquid bottle 1. A gas introducing valve 10 opens/closes a pipe connected between the branch point 9 and the filter 11. A filter 11 has the mesh size of 0.22 μm and has contact with the outside air. A controller 12 controls the pump 6 and the gas introducing valve 10.

The liquid feeder 1 determines the amount of the liquid and feeds the liquid as follows. It is assumed that a flow rate of the pump 6 be Q. When the pump 6 is operated after the gas introducing valve 10 has been closed, the pump 6 feeds the gas in the supply pipe 5, and the liquid in the liquid bottle 2 connected to the gas passes through the supply pipe 5. Then, the liquid feeding is started, and the liquid passes through the branch point 9. An operation time of the pump 6 is a value (time) obtained by dividing a total liquid amount C by a flow rate Q. The total liquid amount C is obtained by adding a target liquid amount A and a volume B (referred to as return amount below) of the pipe corresponding to an amount to the liquid level of the liquid in the liquid bottle 2 from the branch point 9. When the pump 6 is stopped after a predetermined time, the pipe is closed by an internal structure of the pump 6, and the liquid does not move. After that, when the gas introducing valve 10 is opened, the gas is introduced through the filter 11, and the liquid in the supply pipe 5 on the side of the liquid bottle from the position of the branch point 9 (return amount B) returns to the liquid bottle 2 by drop energy of the liquid. The liquid on the side of the pump 6 from the branch point 9 is maintained in a stop state by the internal structure of the pump 6. Next, when the pump 6 is operated for a predetermined time, the gas is sequentially introduced from the filter 11, and the liquid moves in the discharge pipe 7. When the front end of the liquid reaches the receptor 8, and addition of the liquid is started, and the rear end of the liquid reaches the receptor 8, the pump 6 is stopped.

The liquid feeder 1 uses the pump for the dispensation similarly to PTL 2. The liquid such as the liquid culture medium or the cell suspension passes through the pipeline, and the liquid is clogged in the pipeline when the pump is stopped. Similarly, the gas passes through the pipeline in the direction to the culture container so that the liquid culture medium in the pipeline is evacuated. In addition, in this method, gas passes through pipeline to the direction of the liquid bottle for holding the liquid culture medium and the like. Therefore, the liquid such as the liquid culture medium is not maintained in the pipeline.

On the other hand, in the liquid feeding method and the liquid feeder, when the liquid feeding amount is specified by time control calculated based on the flow rate of the pump, there are three problems below.

A first problem is an effect of the liquid level position in the liquid bottle 2 to be a liquid feeding source. When the amount of the liquid held in the liquid bottle 2 is fixed, the liquid level position is fixed. The quantitative property of the total liquid amount C obtained by adding the target liquid amount A and the return amount B is reproduced. It is necessary that the liquid amount C is smaller than the liquid amount held in the liquid bottle. However, since the liquid level in the bottle is positioned higher than usual state when an excess amount of the liquid is held in the liquid bottle, the return amount B is smaller than a predetermined amount. Therefore, the target liquid amount A increases, and the quantitative property of the target liquid amount is reduced. Also, when the liquid is continuously fed, since a holding amount is gradually decreased, the total liquid amount C is gradually decreased. Although the return amount B is changed according to the change of the liquid amount which is held, the liquid amount A generally tends to be decreased.

A second problem is an effect of the liquid level position of the returned liquid. When the liquid level position in the supply pipe 5 is at a fixed position relative to the amount of the liquid held in the liquid bottle 2, the quantitative property of the total liquid amount C obtained by adding the target liquid amount A and the return amount B is reproduced. The liquid level position of the amount of the held liquid is expressed as D, and the liquid level position in the supply pipe 5 is expressed as E. At this time, it is desirable that these positions be consistently fixed. However, when the liquid is returned due to the drop, the positions vertically move in millimeters although D<E is necessarily satisfied. As a result, the variation of the liquid feeding amount gets larger. This is especially remarkable when the liquid bottle at the first liquid feeding is covered and the supply pipe has contact with the liquid. Since the gas introducing valve 10 is closed and the pump 6 is stopped and clogged, the supply pipe 5 is closed other than the opening. When the supply pipe 5 has contact with the liquid in the liquid bottle 2 in this state, the liquid level position exists near the opening of the supply pipe. However, it is difficult to control the liquid level position by using water pressure which fluctuates according to the amount of the held liquid.

A third problem is that it is difficult to specify the pump flow rate. When the flow of the liquid is stable, the flow rate of the pump does not fluctuate. The problem here is remarkable in the example of a roller pump, and the problem is that the pump flow rate is largely changed when the length of the tube to be wound is changed. It is difficult to strictly specify the length of the elastic rubber tube. Specifically, since the tube is disposable when it is used for feeding the liquid by the culture apparatus, it is necessary to frequently exchange the tubes.

A purpose of the present invention is to provide a liquid feeder, which feeds liquid having a target amount by using a pump with high accuracy without keeping liquid culture medium in a pipeline connected to a target container, and a cell culture apparatus for using the same.

Solution to Problem

To solve the problems, the liquid feeder according to the present invention has following characteristics.

The liquid feeder includes a liquid feeding pipe having a liquid introduce port and a liquid discharge port, a housing container which holds liquid to be introduced from the liquid introduce port, a liquid feed mechanism which feeds the liquid in the liquid feeding pipe to the liquid discharge port, a gas introduce unit which introduces gas into the liquid feeding pipe, and a liquid level detection unit which detects an advancing liquid level of the liquid to be fed in the liquid feeding pipe. The gas introduce unit is connected to a branch part provided in the liquid feeding pipe on the upstream side of the liquid feed mechanism. The liquid level detection unit is provided on the downstream side of the branch part.

Advantageous Effects of Invention

According to the present invention, a liquid feeder, which feeds liquid having a target amount by using a pump with high accuracy without keeping liquid culture medium in a pipeline connected to a target container, and a cell culture apparatus for using the same can be provided. According to the liquid feeder of the present invention, an effect of a liquid level position relative to a change of a liquid amount in a liquid bottle which is a liquid feeding source is avoided. Also, an effect of a liquid level position of returned liquid is avoided, and in addition, a change of a pump flow rate caused by an effect of the length of a rubber tube and the like can be avoided.

DESCRIPTION OF EMBODIMENTS

Figure 1:
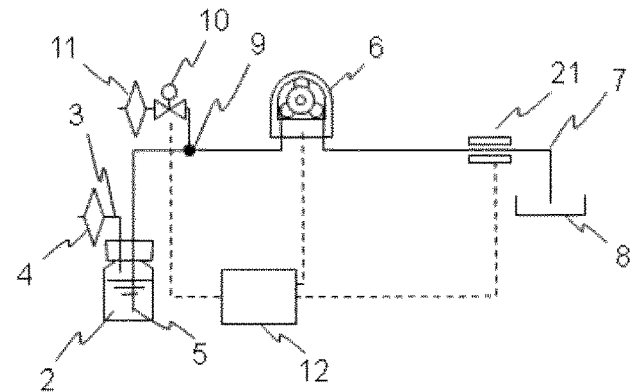
FIG. 1 is a block diagram of a liquid feeder according to a first embodiment.

Various embodiments according to the present invention will be described below with reference to the attached drawings. However, embodiments are just an example to realize the present invention, and the technical scope of the present invention is not limited to the embodiments. Also, components which are common in the drawings are denoted with the same reference numbers.

First Embodiment

A first embodiment of a liquid feeder and a cell culture apparatus for using the same according to the present embodiment will be described below with reference to FIGS. 1 to 8.

<Liquid Feeder>

FIG. 1 is a diagram of a structure of a liquid feeder 20 according to the first embodiment, and the liquid feeder 20 has a basic structure same as that of the conventional apparatus for using a drop of liquid.

A liquid bottle 2 holds the liquid and can airtightly hold the liquid therein with a lid. An air pressure adjusting pipeline 3 is provided in the lid and adjusts air pressure. A filter 4 is provided at an opening end of the air pressure adjusting pipeline 3. The filer 4 has a mesh size of 0.22 µm and is opened to outside air. A supply pipe 5 is provided in the lid and has an opening end in the liquid bottle 2 which has contact with the liquid and becomes a liquid discharge port. One end of a pump 6 is connected to the supply pipe 5, and another end is connected to a discharge pipe 7. A receptor 8 is a target of feeding the liquid. A branch point 9 is provided above the liquid level of the liquid held in the liquid bottle 1. A gas introducing valve 10 opens/closes a pipe connected between the branch point 9 and the filter 11. A solenoid valve is suitable for a valve mechanism used as the gas introducing valve 10. A so-called solenoid valve is a mechanism in which a rubber tube is attached by being sandwiched between parts which is opened/closed by action of an electromagnet and the pipe is opened/closed by elastically deforming the rubber tube by turning ON/OFF the solenoid valve. The valve which will be described below means the solenoid valve.

A liquid level sensor 21 detects whether the liquid exists in the discharge pipe 7. The liquid level sensor 21 is provided at a position having a distance from the branch point 9 which is calculated according to a cross-sectional area of the pipe and a target liquid feeding amount. A filter 11 has the mesh size of 0.22 µm and has contact with the outside air. A controller 12 controls the pump 6, the gas introducing valve 10, and the liquid level sensor 21.

The liquid feeder 20 determines the amount of the liquid and feeds the liquid as follows. It is assumed that a flow rate of the pump 6 be about Q. When the pump 6 is operated after the gas introducing valve 10 has been closed, the pump 6 feeds the gas in the supply pipe 5, and the liquid in the liquid bottle 2 connected to the gas passes through the supply pipe 5. Then, the liquid feeding is started. When the liquid passes through the branch point 9 and the liquid level reaches the position where the liquid level sensor 21 is provided, the pump 6 is stopped. Since the pipe is closed by an internal structure of the pump 6, the liquid does not move.

Next, when the gas introducing valve 10 is opened, the gas is introduced through the filter 11, and the liquid in the supply pipe 5 on the side of the liquid bottle from the position of the branch point 9 (referred to as return amount B) returns to the liquid bottle 2 by drop energy of the liquid. The liquid on the side of the pump 6 from the branch point 9 is maintained in a stop state by the internal structure of the pump 6. The amount of the liquid on the side of the pump 6 is the liquid feeding amount. Next, when the pump 6 is operated for a predetermined time, the gas is sequentially introduced from the filter 11, and the liquid moves in the discharge pipe 7. When the front end of the liquid reaches the receptor 8, and addition of the liquid is started, and the rear end of the liquid reaches the receptor 8, the pump 6 is stopped.

Figure 2:
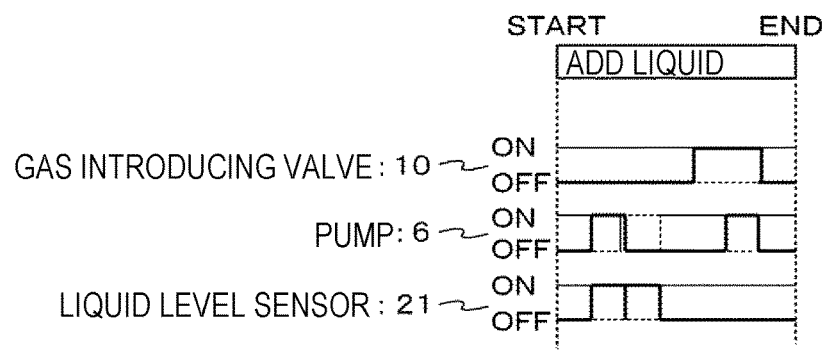
FIG. 2 is a control flowchart of the liquid feeder according to the first embodiment.
Figure 3:
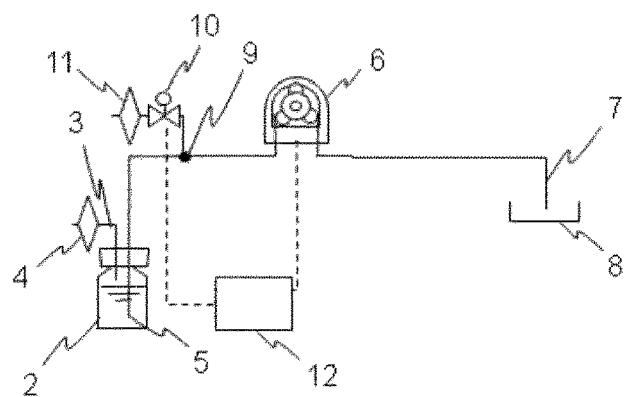
FIG. 3 is a diagram of a structure of a liquid feeder in the related art.

FIG. 2 is a control flowchart of the first embodiment. The lateral direction of this chart indicates a time axis, and the vertical direction indicates ON/OFF states of the gas introducing valve 10, the pump 6, and the liquid level sensor 21 illustrated in FIG. 1.

First, the pump 6 is operated at the time of "START", and the liquid feeding is started. When the front end of the liquid reaches the liquid level sensor 21, the operation of the pump 6 is immediately stopped in response to a signal from the liquid level sensor. Next, the gas introducing valve 10 is opened. The pump 6 is operated for a period which is set to be longer than time until the rear end of the liquid reaches the receptor 8, and the gas introducing valve 10 is closed after arbitrary time.

In a case where the liquid feeder 20 according to the first embodiment is used, a liquid level can be managed to be a position of the liquid level sensor 21 by feeding the liquid by the pump even when the liquid level position in the liquid bottle 2 that is a liquid feeding source is at any positions in the supply pipe 5. This is because the liquid feeding amount is equal to a volume managed by a product of a cross-sectional area of the pipe and a distance of the liquid level sensor 21 which is placed at a calculated distance from the branch point 9 according to the target liquid feeding amount, and the amount of the liquid of which the rear end is positioned at the branch point 9 and the front end is positioned at the liquid level sensor 21 at the time of introducing the gas is the liquid feeding amount.

When the liquid feeder 20 is used, the liquid level can be managed to be the position of the liquid level sensor by feeding the liquid by the pump regardless of the liquid level position of returned liquid in the liquid bottle 2. Therefore, according to the same reason, the liquid feeding amount can be controlled, and an effect of the liquid level position of the returned liquid at the time when the liquid is continuously fed can be avoided.

When the liquid feeder 20 is used, the liquid feeding amount is not controlled based on the pump operation time obtained from the pump flow rate. The liquid feeding amount is equal to the volume managed by the product of the cross-sectional area of the pipe and the distance of the liquid level sensor 21 which is placed at the calculated distance from the branch point 9 according to the target liquid feeding amount, and the liquid has the rear end positioned at the branch point 9 and has the front end positioned at the liquid level sensor 21 at the time of introducing the gas. Therefore, a change of the pump flow rate due to an effect by the length of the rubber tube and the like can be avoided.

A roller pump is suitable for the pump 6. However, pumps of other types such as a diaphragm pump and a gear pump can be applied to the pump 6. The roller pump which is a so-called squeezing pump and tube pump is a mechanism for feeding the gas and liquid in the rubber tube by winding the rubber tube around the roller attached to a motor rotating shaft and elastically deforming the rubber tube by a motor rotation. In the cell culture apparatus, it is necessary to secure sterilization properties of the tube for feeding the liquid. The roller pump of which the tube can be exchanged at the time of the usage is useful. Any liquid feeding pumps can be used when the sterilization can be performed to the inside of the pump at the time of the usage.

Also, it is necessary to have a structure in which the liquid in the pump at the time of stopping the pump. However, at the time of using the pump in which the liquid moves, the pump can be applied to the present invention when a pipeline is configured to have a check valve, which limits the flow of the liquid to the side of the liquid feeding bottle, provided in the front/rear of the pump.

Figure 4:
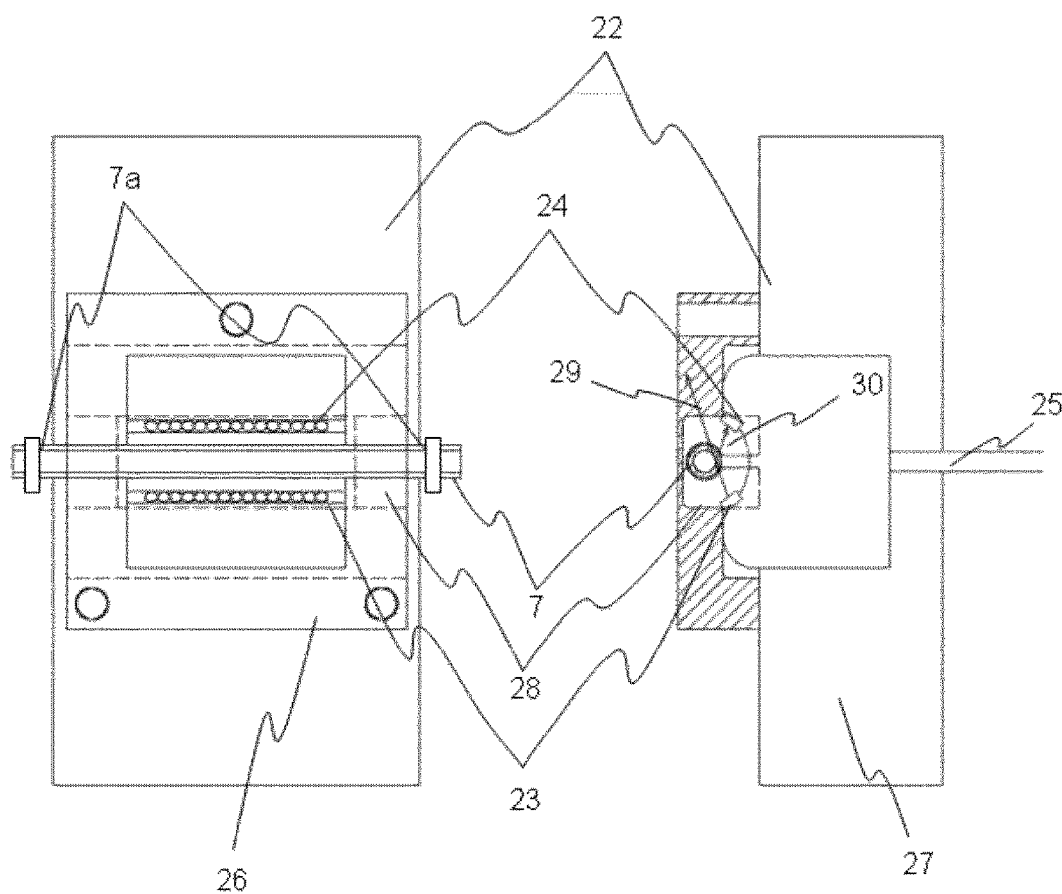
FIG. 4 is a diagram of a liquid level sensor according to the first embodiment.

FIG. 4 is a block diagram of the liquid level sensor 21 and the liquid feeding pipe 7. A top view is illustrated on the left side of the main view, and a side view is illustrated on the right side. The description will be made with reference to the top view and the side view. A liquid level sensor body 22 includes a plurality of light sources 23, light receiving windows 24 respectively corresponding to the light sources 23, and a signal line 25 connected to the controller 12 (refer to FIG. 1). The light source 23 and the light receiving window 24 are provided in parallel to the liquid feeding pipe 7 which transmits light. In addition, in order to detect the liquid level in the liquid feeding pipe 7 at high reproducibility, an installation tool 26 and an installation base 27 are included. These are removable and fixed with a screw and the like when they are used. When the installation tool 26 holds a detection part of the liquid feeding pipe 7 between two pipe fixing units 28 and fixes the liquid feeding pipe, the liquid feeding pipe 7 is held at a distance where a light receiving amount of the light receiving window 24 is optimal. The light receiving window 24 receives detection light 29 emitted from the light source 23 in the liquid level sensor and reflection light 30 from a wall in the liquid feeding pipe 7. A mark 7a is provided in the liquid feeding pipe and is attached at a position which has been previously calculated so that the installation tool 26 is placed at a position corresponding to the target liquid amount.

The liquid level sensor 21 detects whether the liquid exists as follows. When the liquid does not exist in the liquid feeding pipe 7, the detection light 29 has a large difference between refraction indexes of the wall in the pipe and air, and the light receiving window 24 receives much detection light 29. When the liquid is fed in the liquid feeding pipe, the difference between the refraction indexes of the wall in the pipe and the liquid of the detection light 29 decreases, and the detection light 29 travels in the liquid. Then, the amount of the detection light 29 received by the light receiving window 24 decreases. The controller 12 determines a signal value according to the light receiving amount and can detect existence of the liquid to be fed to the liquid feeding pipe 7 when the light receiving amount is reduced.

It is preferable to have a plurality of light sources 23 and a plurality of light receiving windows 24 corresponding to the light sources 23. There is a case where the front end of the fed liquid includes fine bubbles, and there is a possibility to wrongly determine the existence of the liquid. However, when the plurality of light sources 23 and light receiving windows 24 corresponding to the light sources 23 are included and they are placed in parallel in the length direction of the pipe, a vapor phase (bubble), a liquid phase mixed with the vapor phase (bubble), and a liquid flow including the liquid phase are detected by using continuous light amount changes, and an effect to reduce the possibility of wrong detection can be obtained.

In addition, a case can be considered in which little residual liquid of the previous time is flown by being formed into small knots of liquid, such as a case where the liquid is fed to another receptor by using the same liquid feeding pipe. When the knots are generated in the front side of the liquid flow which is a target liquid feeding amount, possibility to wrongly detect the liquid level increases. Even in this case, when the plurality of light sources 23 and light receiving windows 24 corresponding to the light sources 23 are included and they are placed in parallel in the length direction of the pipe, the light amount to determine the front end of the target liquid level by only using the knot of the liquid cannot be obtained. Therefore, an effect to reduce the possibility of wrong detection can be obtained.

On the other hand, it is preferable to have a plurality of liquid level sensors 21 relative to the liquid feeding pipe to improve reliability of the liquid feeder. When two or more liquid level sensors are provided, one is a liquid level sensor for determining the amount which is placed at a distance calculated from the branch point 9 according to the target liquid feeding amount, another one is a wrong detection liquid level sensor. The wrong detection liquid level sensor is placed at a position closer to the liquid feeding source than the liquid level sensor for determining the amount, and the wrong detection liquid level sensor alone does not stop feeding the liquid by the pump. When a special large knot which causes the wrong detection is generated, the large knot passes through the wrong detection liquid level sensor. When the large knot reaches the liquid level sensor for determining the amount, the feeding of the liquid by the pump is stopped. At this time, a liquid level sensor for knot detects the vapor phase in many cases, and there is high possibility that the sensor does not detect a true liquid passage state. That is, when both the wrong detection liquid level sensor and the liquid level sensor for determining the amount do not normally detect the liquid, it is determined that the state is wrong liquid feeding.

In a state where the liquid is fed and the wrong detection is generated as described above, there may be cases in which an amount of the held liquid in the liquid bottle is not enough. Therefore, when the wrong detection occurs, it is desirable to stop feeding the liquid. That is, when a liquid level detection unit is used, it is effective as a method to prevent the liquid from being fed under the conditions of a set up failure by an operator and a malfunction of the liquid feeder. For example, when information on time when the liquid is started to be fed to the pump and time when the liquid reaches the liquid level is used, information on the flow rate of the pump to be used can be obtained. Alternatively, even in an abnormal starting state in which a valve which should be closed is opened and a valve which should not be closed is closed, when the liquid does not reach the liquid level at expected liquid level reaching time, it can be understood that some failures occur.

In this liquid feeder, when it is desired to feed the liquid of two or more liquid feeding amounts, it is preferable to place a plurality of liquid level sensors which is placed at a distance calculated from the branch point 9 according to a plurality of target liquid feeding amounts. Also, the maximum amount of the liquid feeding amount of a single operation does not exceed the length of the liquid feeding pipe. However, when a large liquid feeding amount that exceeds the length of the liquid feeding pipe is requested, it is preferable to perform a plurality of times of liquid feeding operations.

A sensor for using characteristics of light is suitable for the liquid level sensor used in the present embodiment.

However, a pressure sensor, an ultrasonic sensor, and a strain sensor can be used, and the sensor is not limited to the above.

In this liquid feeder, when the liquid of the same liquid amount is fed to the plurality of receptors, the branch points, of which the number is corresponding to that of the receptors, and container switching valves corresponding to the branch points are provided between the pump 6 and the receptor 7, and the container switching valve through which the liquid is fed is opened, and this operation is repeated. Then, since the liquid of the same amount is fed and a liquid culture medium is not maintained in the pipeline in this section, there is no possibility that the pipe is clogged.

In addition, the liquid feeder can feed the liquid while stirring the liquid. This is because convection is generated relative to the held liquid which has been static in the liquid bottle when the returned liquid is generated by introducing the gas. This effect is remarkable when the liquid to be fed has an uneven liquid composition. For example, in cell suspension in which the cells are suspended in the culture medium, the convection is generated in the liquid by pushing/pulling a piston of a dispenser before cell seeding in a case of a manual operation, and a stirring operation is operated. When the liquid feeder seeds the cells in a plurality of culture containers, the returned liquid is generated and the liquid is stirred at every liquid feeding. When it is desired to more effectively stir the liquid, after the gas introducing valve 10 has been closed in FIG. 1, the front end of the liquid in the liquid bottle 2 is stopped before the branch point 9 by operating the pump 6. Next, the gas introducing valve 10 is opened, and accordingly, the returned liquid is generated, and a single stirring process is completed. When the plurality of processes is continuously performed, the liquid can be more effectively stirred.

With the liquid feeding method by the pump, an effect of a viscous resistance and temperature derived from the liquid composition generated by the liquid flow in the pipe and an effect of a drop according to bentness in the pipe and upper and lower positional relation between the containers often fluctuate the flow rate of the pump, and quantitative property of the liquid feeding is deteriorated. When the liquid feeder 20 is used, since the liquid feeding amount is defined according to the described method, the liquid can be fed while avoiding the change of the pump flow rate according to the condition of the liquid flow. That is, even when the temperature of the fed liquid is changed and when the number of the branches and arrangement of the containers are changed by the increase in the number of the receptors, the liquid can be fed while securing a constant quantitative property.

<Structures of Cell Culture Container and Automatic Cell Culture Apparatus>

Figure 5:
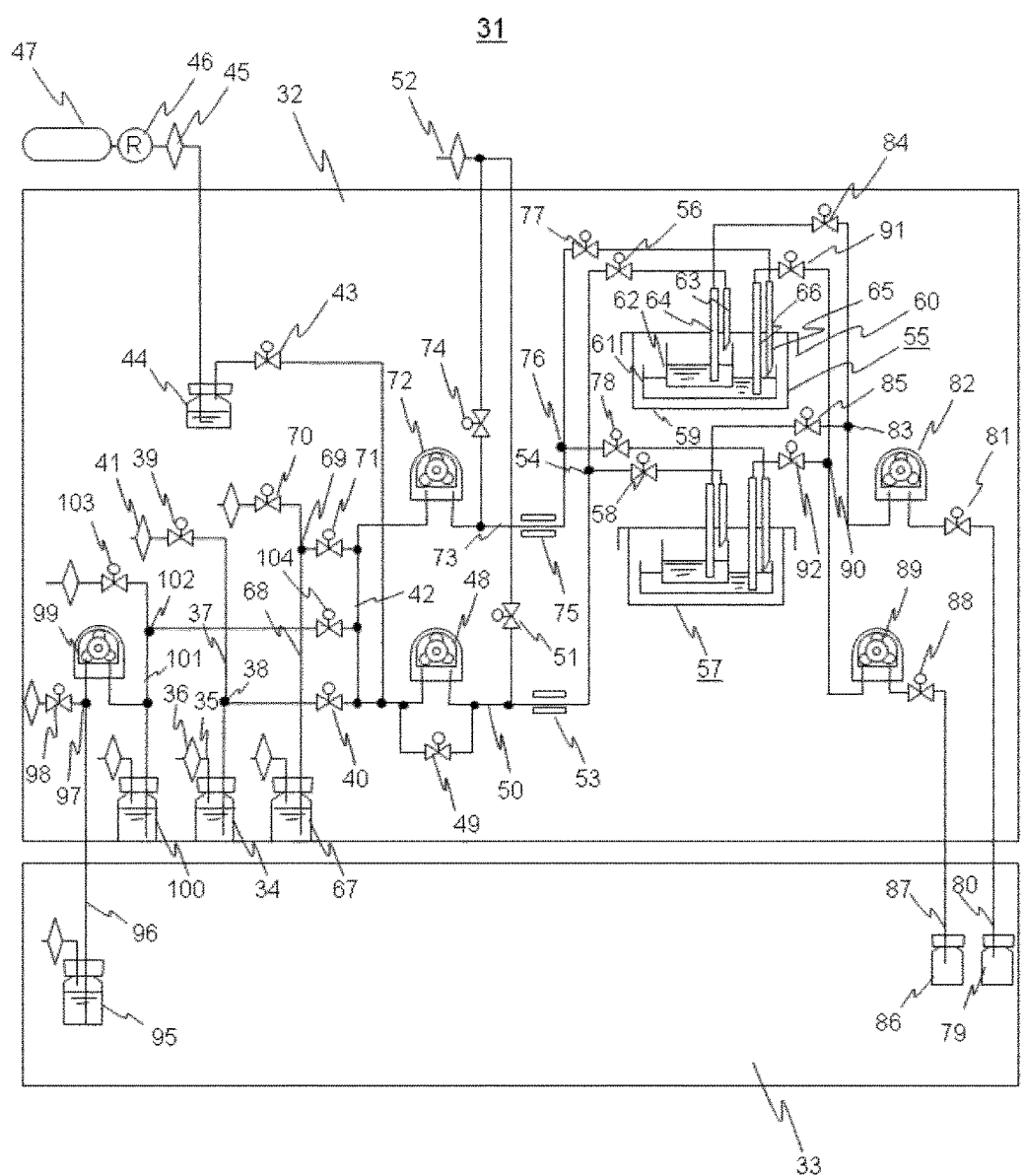
FIG. 5 is a block diagram of a cell culture apparatus and the liquid feeder according to the first embodiment.

FIG. 5 is a diagram of an exemplary automatic cell culture apparatus 31 for using the liquid feeder 20 according to the first embodiment. The embodiment will be described below by using an automatic cell culture apparatus including a liquid feeding control unit for supplying and discharging the liquid culture medium to the cell culture container. A thermostatic chamber 32 holds a cell culture container at an optimal culture temperature for culturing cells. A refrigerator 33 holds components to be held at a cool temperature.

A first cell bottle 34 holds first cell suspension and can be airtightly hold it therein with a lid. A pipeline 35 is provided in one of the lids and adjusts air pressure. A filter 36 is provided at an opening end and has a mesh size of 0.22 µm. The filter 36 is opened to outside air in the thermostatic chamber 32. A supply pipe 37 is provided in the lid and has an opening end in the first cell bottle 34 which has contact with the cell suspension and becomes a liquid discharge port. The supply pipe 37 is branched into two pipes via a branch point 38. One of the pipes is connected to a first gas introducing valve 39, and another supply pipe 37 is connected to a first cell switching valve 40. The branch point 38 is provided above the liquid level of the liquid held in the liquid bottle 34. A filter 41 is provided at an opening end and has a mesh size of 0.22 µm. The filer 41 is opened to the outside air in the thermostatic chamber 32.

The first cell switching valve 40 is branched into two pipes. One of the pipes is connected to a common pipe 42 (common pipe 42 will be described below), and another pipe is connected to a branch leading to a first gas switching valve 43. The first gas switching valve 43 is connected to a humidifying bottle 44, and the humidifying bottle 44 is connected to a filter 45 having a mesh size of 0.22 µm. A mixture gas cylinder 47 including $CO_2$ and $O_2$ is connected to the upstream of the pressure control valve 46. The $CO_2$ gas is pressurized at an optimal gas concentration.

In order to prevent that the pH value of the liquid culture medium culturing the cells is changed with time, it is necessary to regularly exchange the gas from the surface of the liquid culture medium with the $CO_2$ gas. In addition, it is necessary to prevent concentration of liquid culture medium components due to evaporation of the liquid culture medium. The $CO_2$ gas derived from the gas cylinder 47 is humidified at the optimum humidity and waits in the humidifying bottle 44.

Another supply pipe 37 of two branches connected to the first gas switching valve 43 is branched into a suction port of a first pump 48 and a second gas switching valve 49. A discharge port of the first pump 48 and the second gas switching valve 49 are integrated into a discharge pipe 50. That is, the second gas switching valve 49 has a role as a bypass of the first pump 48. Here, a pipe for feeding the liquid between the suction port of the pump and the cell bottle is a supply pipe, and a pipe for feeding the liquid between the discharge port of the pump and the receptor for culturing the cells is a discharge pipe.

The discharge pipe 50 is branched into two pipes. One end of the two pipes is connected to a filter 52 via a first exhaust switching valve 51, and another connection port of the filter 52 is opened to outside air. On another end of the discharge pipe 50, a first liquid level sensor 53 which is a structure of the optical sensor 21 described in FIG. 4 is provided. Also, the first liquid level sensor 53 is provided at a calculated distance from the branch point 38 where the amount of the first cell suspension reaches a desired liquid amount. Subsequently, the discharge pipe 50 is branched at a multi-branch unit 54 and is connected to a first container switching valve 56 for a first culture container 55 and a first container switching valve 58 for a second culture container 57. Since both the first culture container 55 and the second culture container 57 have the same structure, the description will be made below with reference to the first culture container 55.

An external appearance of the first culture container 55 includes a main body part 59 and a lid part 60, and the first culture container 55 is an airtight container. An internal appearance can hold a second container 61 which can hold the cells in an internal bottom part of the main body part 59 and can culture the cells and a first container 62 which can hold and culture the cells.

A culturing surface of the first container 62 is formed of a substance permeable film and transmits growth factors produced from the vegetative cells cultured in the second container 61. The first container 62 is a culture container for performing a culture method (cocultivation) for promoting the growth of cells cultured in the first container. The lid part 60 has four ports for passing therethrough. A first port 63 adds the liquid to the first container 62, and a second port 64 has contact adjacent to the bottom surface of the first container 62 and discharges the liquid. A third port 65 adds the liquid to the second container 61, and a fourth port 66 has contact adjacent to the bottom surface of the second container 61 and discharges the liquid.

The discharge pipe 50 is connected to the first port 63 via the first container switching valve 56. That is, in a piping structure, the cell suspension in the first cell bottle 34 is fed to the first container 62 of the first culture container 55 or the second culture container 57 by the action of the first pump 48.

A second cell bottle 67 holds second cell suspension. A lid, a pipeline to adjust the air pressure, a filter, and a supply pipe 68 are the same as those in the first cell bottle 34, and accordingly, the description will be omitted. Similarly, a connection structure between the supply pipe 68, a branch point 69, a second gas introducing valve 70, and a second cell switching valve 71 is the same as that of the first cell bottle 34.

The supply pipe 68 is branched into two pipes via the second cell switching valve 71. One of the pipes is connected to the common pipe 42, and another pipe is connected to a suction port of a second pump 72. A discharge pipe 73 extended from a discharge port of the second pump 72 is branched into two pipes. One of the pipes is connected to the filter 52 via a second exhaust switching valve 74, and a second liquid level sensor 75 is provided at another end of the discharge pipe 73 and is placed at a calculated distance from the branch point 69 where the second cell suspension reaches a desired liquid amount.

Subsequently, the discharge pipe 73 is branched at a multi-branch unit 76 and is connected to a second container switching valve 77 for the first culture container 55 and a second container switching valve 78 for the second culture container 57. The second container switching valve 77 is connected to the third port for adding the liquid to the second container 61. That is, in a piping structure, the cell suspension in the second cell bottle 67 is fed to the second container 61 of the first culture container 55 or the second culture container 57 by the action of the second pump 72.

A culture medium bottle 95 holds a spare liquid culture medium and is held in the refrigerator 33. A lid, a pipeline to adjust the air pressure, a filter, and a supply pipe 96 are the same as those in the first cell bottle 34. Similarly, a connection structure between a supply pipe 96, a branch point 97, and a third gas introducing valve 98 is the same as that of the first cell bottle 34. A suction port of a fifth pump 99 is connected to the supply pipe 96. A culture medium preheating bottle 100 holds a required amount of the spare liquid culture medium and connected to a discharge port of the fifth pump 99 by a supply pipe 101 via a branch. The culture medium preheating bottle 100 is held in the thermostatic chamber 32. That is, in the piping structure, the liquid culture medium in the culture medium bottle 95 is fed to the culture medium preheating bottle 100 by the action of the fifth pump.

A lid, a pipeline to adjust air pressure, a filter, and the supply pipe 101 of the liquid culture medium held in the culture medium preheating bottle 100 are the same as those in the first cell bottle 34, and accordingly, the description will be omitted. Similarly, a connection structure between the supply pipe 101, a branch point 102, a fourth gas introducing valve 103, and a culture medium switching valve 104 is the same as that of the first cell bottle 34. The supply pipe 101 is connected to the common pipe 42 and branched. One end is connected to the supply pipe 37 extended from the first cell bottle 34 via the first cell switching valve 40, and another end is connected to the supply pipe 68 extended from the second cell bottle 67 via the second cell switching valve 71.

That is, the common pipe 42 is connected to three switching valves, i.e., the first cell switching valve 40, the second cell switching valve 71, and the culture medium switching valve 104. Regarding the piping structure, in a case where the first pump 48 acts, the liquid in the first cell bottle 34 is fed to the first container 62 in the first culture container 55 or the second culture container 57 when the first cell switching valve 40 is opened. In a case where the second pump acts, the liquid in the second cell bottle 67 is fed to the second container 61 in the first culture container 55 or the second culture container 57 when the second cell switching valve 71 is opened. In a case where the first pump 48 acts, the liquid culture medium held in the culture medium preheating bottle 100 is fed to the first container 62 in the first culture container 55 or the second culture container 57 when the culture medium switching valve 104 is opened. In a case where the second pump acts, the liquid culture medium held in the culture medium preheating bottle 100 is fed to the second container 61 in the first culture container 55 and the second culture container 57 when the culture medium switching valve 104 is opened.

It is necessary to consider the volumes of pipes which are connected from the first pump 48, the second pump 72, and other branches between the branch point 38, the branch point 69, and the branch point 102 and the first liquid level sensor 53, and the second liquid level sensor 75 in FIG. 5. However, when a solenoid valve is provided on extended lines of the other branches and closed, the flow of the liquid is not substantially generated. Therefore, as a distance of the liquid level sensor which defines the liquid feeding amount, it is preferable to consider the shortest distance between a branch point and the liquid level sensor of the liquid to pass through.

A structure for discharging the held liquid from the first culture container 55 or the second culture container 57 will be described. A first drainage bottle 79 is airtightly connected to a drain pipe 80. The drain pipe 80 is connected to a discharge port of a third pump 82 via a first discharge valve 81. A suction port of the third pump 82 is branched by a multi-branch unit 83 and connected to a first container discharge valve 84 for the first culture container 55 and a first container discharge valve 85 for the second culture container 57. The first container discharge valve 84 is connected to the second port 64 of the first culture container 55. That is, in the piping structure, the liquid in the first drainage bottle 79 is discharged from the first container 62 of the first culture container 55 or the second culture container 57 by the action of the third pump 82.

A second drainage bottle 86 is airtightly connected to a drain pipe 87. The drain pipe 87 is connected to a discharge port of a fourth pump 89 via a second discharge valve 88. A suction port of the fourth pump 89 is branched by a multi-branch unit 90 and connected to a second container discharge valve 91 for the first culture container 55 and a second container discharge valve 92 for the second culture container 57. The second container discharge valve 91 is connected to the fourth port 66 of the first culture container 55. That is, in the piping structure, the liquid in the second drainage bottle 85 is discharged from the second container 59 of the first culture container 55 or the second culture container 57 by the action of the fourth pump 89.

<Operation for Culturing Cells and Observation Operation>

Figure 6:
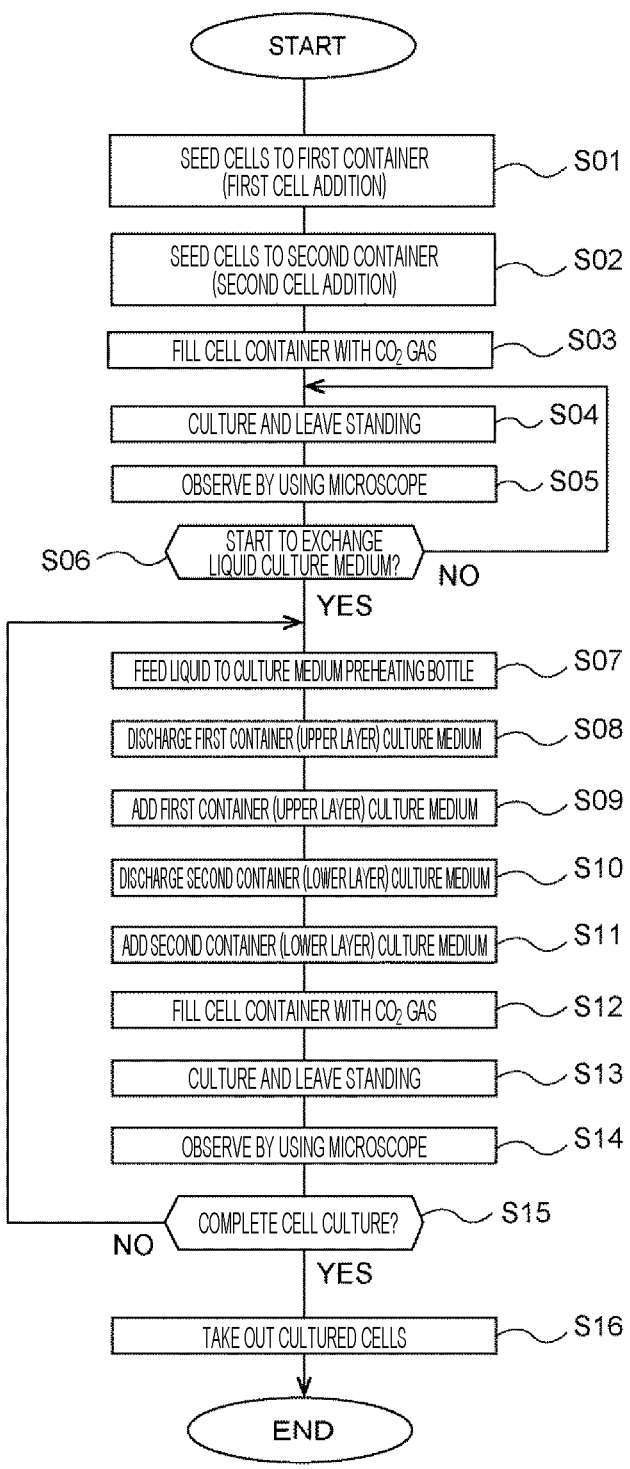
FIG. 6 is a control flow of an automatic culture apparatus according to the first embodiment.

FIG. 6 is a flowchart of a whole operation for culturing cells and an observation operation in the cell culture apparatus controlled by a controller which is not shown. First, cell seeding (first cell addition) is performed to the first container 62 of the culture container (S01), and the cell seeding (second cell addition) is performed to the second container 61 (S02). When a plurality of cell cultures is performed, the above operation is repeated. In addition, after filling the $CO_2$ gas into the cell culture container (S03), the cells are cultured and are left standing (S04). The observation by using a microscope is performed (S05), and it is determined whether to start to exchange the liquid culture medium (S06). When the liquid culture medium is exchanged, after the liquid is fed to the culture medium preheating bottle (S07), first container culture medium discharge (S08), first container culture medium addition (S09), second container culture medium discharge (S10) and second container culture medium addition (S11) are performed. In addition, after filling the $CO_2$ gas into the cell culture container (S12), the cells are cultured and are left standing (S13). The observation by using the microscope is performed (S14), and it is determined whether the cell culture is completed (S15). When the cell culture has been completed, the cultured cells are taken out (S16).

Figure 7A:
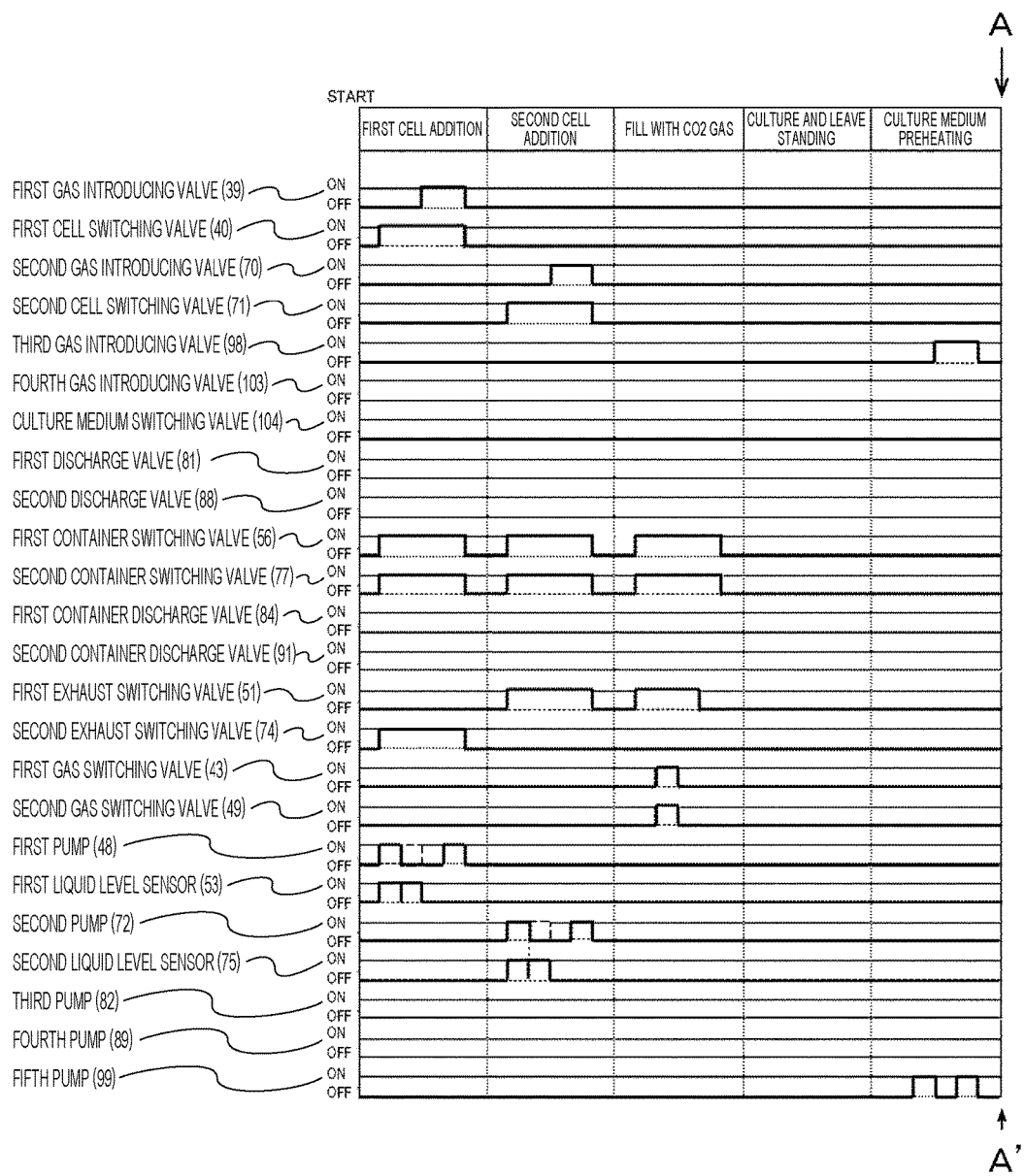
FIG. 7A is a control flowchart according to the first embodiment.
Figure 7B:
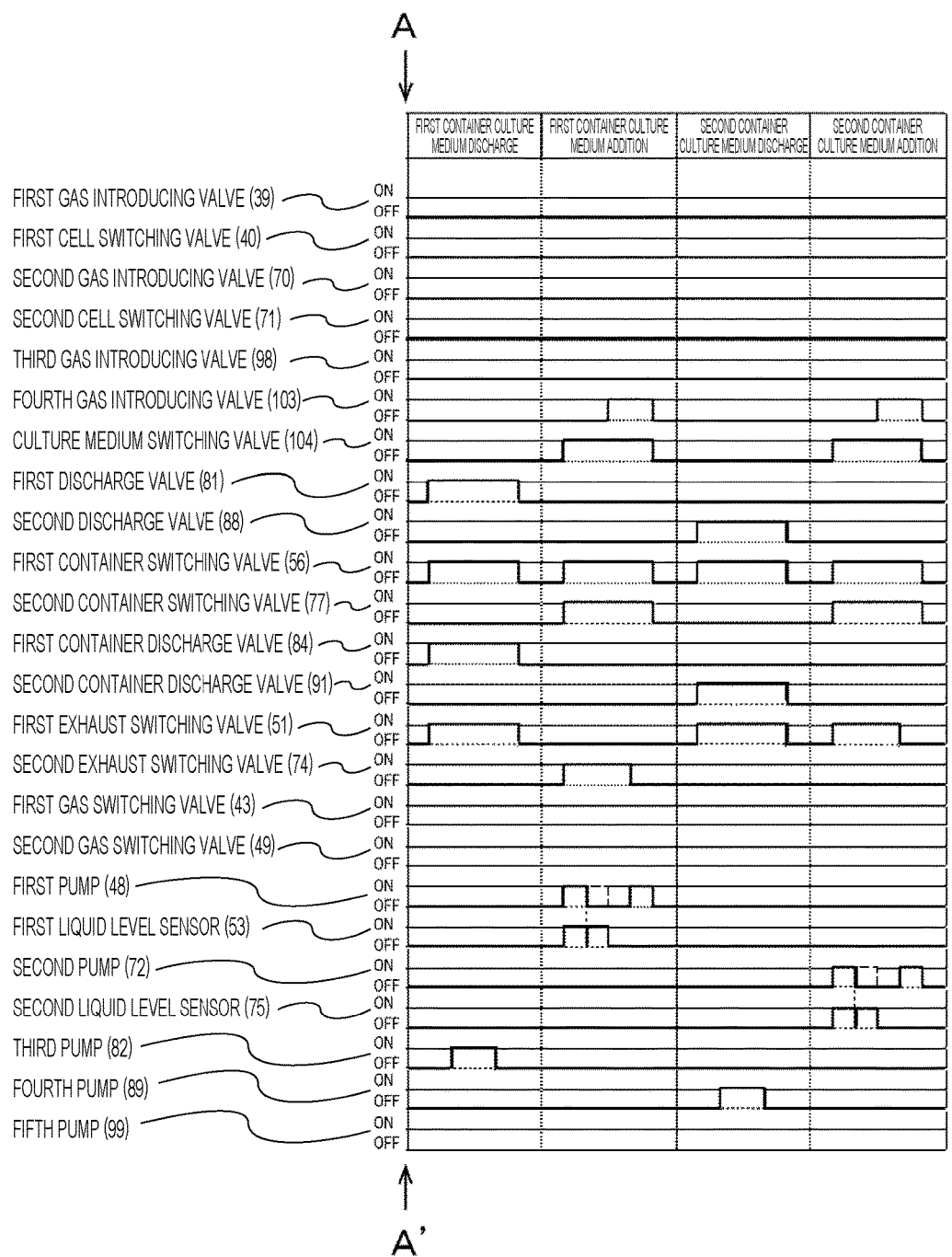
FIG. 7B is a control flowchart according to the first embodiment.

FIGS. 7A and 7B are time charts of liquid and gas feeding in the first culture container 55 controlled by a controller which is not shown. The horizontal axis indicates operation items and a time axis. The vertical direction indicates operation timings of 19 solenoid valves from the first gas introducing valve 39 to the culture medium switching valve 104, five roller pumps from the first pump 48 to the fifth pump 99, the first liquid level sensor 53, and the second liquid level sensor 75 which have been clearly described in FIG. 5. In the initial state, all the valves are turned OFF and closed, and all the pumps are turned OFF. Therefore, the liquid feeding is stopped. For convenience of illustration, FIGS. 7A and 7B are divided by a line A-A' and displayed. However, it is assumed that the time axes of the horizontal axes in FIGS. 7A and 7B are connected to each other.

When the cells are seeded to the first container 62 in the cell culture container 55 (S01 in FIG. 6), the operation is performed according to the operation of the first cell addition. When the first cell switching valve 40, the first container switching valve 56, the second container switching valve 77, and the second exhaust switching valve 74 are turned ON at an initial state and these valves are opened, the first cell bottle 34 is communicated with the first cell switching valve 40 and the first container switching valve 56, and a flow passage to the first port 63 is communicated. Also, the filter 52 communicated with outside air is communicated with the second exhaust switching valve 74 and the second container switching valve 77, and a pipeline from the filter connected to the outside air to the third port 65 is communicated. Subsequently, when the first pump 48 is turned ON for a predetermined time, the feeding of the cell suspension from the first cell bottle 34 is started, and the front end of the cell suspension reaches the first liquid level sensor 53. When a liquid level detection signal is output from the first liquid level sensor 53, the first pump 48 stops feeding the liquid. Next, when the first gas introducing valve 39 is opened, a cell suspension, of which the amount is determined, having the branch point 38 as the rear end and the first liquid level sensor 53 as the front end is created in the supply pipe 37. Subsequently, when the first pump 48 starts to feed the liquid, the cell suspension is fed from the first port 63 of the cell culture container 55 through the first container switching valve 56. At this time, since the third port 65 is communicated with the outside air, pressure in the cell culture container 55 is adjusted to be a normal pressure. After a predetermined amount of the liquid has been injected, the liquid feeding is terminated by stopping the first pump 48 and closing and turning OFF the opened valves.

When there is a plurality of cell culture containers, the cell suspension having an amount which can be distributed to the plurality of cell culture containers is previously held in the first cell bottle 34, and the first container switching valve 56 is closed by the above operation. The first container switching valve 58 in FIG. 5 is opened, and the second container switching valve 77 is closed, and the second container switching valve 78 in FIG. 5 is opened. After that, when the above operation is performed, the same amount of the cell suspension is fed to the first container 62 of the cell culture container 57.

Next, when the cells are seeded to the second container 61 in the cell culture container 55 (S02 in FIG. 6), the operation is performed according to the operation of the second cell addition. When the second cell switching valve 71, the first container switching valve 56, the second container switching valve 77, and the first exhaust switching valve 51 are turned ON at an initial state and these valves are opened, the second cell bottle 67 is communicated with the second cell switching valve 71 and the second container switching valve 77, and a flow passage to the third port 65 is communicated. Also, the filter 52 communicated with outside air is communicated with the first exhaust switching valve 51 and the first container switching valve 56, and a pipeline from the filter connected to the outside air to the first port 63 is communicated. Subsequently, when the second pump 72 is turned ON for a predetermined time, the feeding of the cell suspension from the second cell bottle 67 is started, and the front end of the cell suspension reaches the second liquid level sensor 75. When a liquid level detection signal is output from the second liquid level sensor 75, the second pump 72 stops feeding the liquid. Next, when the second gas introducing valve 70 is opened, cell suspension, of which the amount is determined, having the branch point 69 as the rear end and the second liquid level sensor 75 as the front end is created in the supply pipe 68. Subsequently, when the second pump 72 starts to feed the liquid, the cell suspension is fed from the third port 65 of the cell culture container 55 through the second container switching valve 77. At this time, since the first port 63 is communicated with the outside air, pressure in the cell culture container 55 is adjusted to be a normal pressure. After a predetermined amount of the liquid has been injected, the liquid feeding is terminated by stopping the second pump 72 and closing and turning OFF the opened valves.

When there is a plurality of cell culture containers, the cell suspension having an amount which can be distributed to the plurality of cell culture containers is previously held in the second cell bottle 67, and the second container switching valve 77 is closed by the above operation. The second container switching valve 78 in FIG. 5 is opened, and the first container switching valve 56 is closed, and the second container switching valve 58 in FIG. 5 is opened. After that, when the above operation is performed, the same amount of the cell suspension is fed to the second container 61 of the cell culture container 57.

Next, when the cell culture container 55 is filled with $CO_2$ gas (S03), the operation is performed according to the operation for filling $CO_2$ gas. When the first container switching valve 56, the second container switching valve 77, the second gas switching valve 49, and the second exhaust switching valve 74 are turned ON at the initial state and these valves are opened, the first gas switching valve 43 is communicated with the first container switching valve 56, and a flow passage to the first port 63 is communicated. Also, the filter 52 is communicated with the second exhaust switching valve 74 and the first container switching valve 77, and a flow passage to the third port 65 is communicated. Subsequently, when the first gas switching valve 43 is turned ON for a predetermined time, $CO_2$ gas moves from the gas cylinder 47 and passes through the humidifying bottle 44. The $CO_2$ gas which has been optimally humidified reaches the cell culture container 55 from the first container switching valve 56 via the first port 63. Although the cell culture container 55 is sealed, a section from the third port 65 to the filter 52 communicating to the outside air is opened. Therefore, a pressure in the cell container is adjusted relative to the outside air pressure. After a predetermined amount of $CO_2$ gas has been injected, the first gas switching valve 43 is closed first, and subsequently, the second gas switching valve 49 is closed. Then, when the pressure in the culture container is equivalent to the atmospheric pressure, other valves are closed.

When there is a plurality of cell culture containers, the second container switching valve 77 is closed by the above operation, and the second container switching valve 78 in FIG. 5 is opened. The first container switching valve 56 is closed, and the second container switching valve 58 in FIG. 5 is opened. After that, when the above operation is performed, the cell culture container 57 is filled with $CO_2$ gas.

Regarding the cell culture, the first container 62 holds the first cell suspension, and the second container 61 holds the second cell suspension. Also, the $CO_2$ gas which is optimally humidified is held in the inner space of the cell culture container 55, and the cell culture container 55 is kept at the optimal culture temperature. Accordingly, the cell culture is continued by leaving them still and holding them for a predetermined time (S04). The cells in the cell suspension are bonded to the upper part of a substance permeable film of the first container 62 or the bottom surface in the second container 61 and grow. Therefore, the liquid culture medium of which the components are changed according to be cultured can be separated from the cells and discharged.

Cell observation during the cell culture (S05) is performed by using a microscopic observation unit which is not shown during the operation for culturing and leaving standing the cells. A phase contrast microscope is preferable for microscopic observation. However, and optical microscope such as an inverted optical microscope may be used. When the microscope has an imaging function, a cell observation process during at the time of culturing the cells can be recorded, and the cell culture can be more preferably performed.

Next, when the liquid culture medium in the cell culture container is exchanged (S06), the operation is performed according to the operations in the operation time chart in FIG. 6. The operations include liquid feeding for the culture medium preheating, the first container culture medium discharge, the first container culture medium addition, the second container culture medium discharge, and the second container culture medium addition. When the liquid is fed for the culture medium preheating to preheat the liquid culture medium (S07), the culture medium bottle 95 is communicated with the culture medium preheating bottle 100 via the fifth pump 99 in the initial state. The culture medium preheating bottle 100 is connected to the filter which communicates with the outside air from the lid. Therefore, the liquid feeding is started while giving a pump operation time to the fifth pump 99. The pump operation time corresponds to the total liquid feeding amount obtained by adding a target amount and the volume of the supply pipe 96 from the branch point 97 to the culture medium bottle 95. After a predetermined time has elapsed, the liquid culture medium on the downstream of the branch point 97 returns to the culture medium bottle 95 when the third gas introducing valve 98 is opened. The liquid culture medium, of which the amount is determined, having the branch point 97 as the rear end and the culture medium preheating bottle 100 as the front end is created in the supply pipe 96. Subsequently, when the fifth pump 99 starts to feed the liquid, the liquid culture medium is fed in the culture medium preheating bottle 100. At this time, since the culture medium preheating bottle 100 is communicated with the outside air, the pressure in the culture medium preheating bottle 100 is adjusted to be a normal pressure. After a predetermined amount of the liquid has been injected, the liquid feeding is terminated by stopping the fifth pump 99 and closing and turning OFF the opened valves.

When there is a plurality of cell culture containers, the liquid feeding amount of the pump is adjusted so that the liquid culture medium having the amount which can be distributed to the plurality of cell culture containers is previously held in the culture medium preheating bottle 100. Also, when a plurality of times of exchanges of the culture medium in the cell culture is scheduled, the liquid culture medium is held in the culture medium bottle. The amount of the liquid culture medium is enough for feeding the liquid culture medium having the amount obtained by multiplying a necessary amount of the liquid culture medium for the plurality of cell culture containers with the number of times of the exchanges of the culture medium. Accordingly, the plurality of times of exchanges of the culture medium can be performed relative to the plurality of cell culture containers.

When the culture medium is discharged from the first container 62 in the cell culture container 55 (S08), the operation is performed according to the first container culture medium discharge operation in operation time charts in FIGS. 7A and 7B. When the first container switching valve 56 and the first exhaust switching valve 51 are turned ON at the initial state, the first container discharge valve 84, the first discharge valve 81, and these valves are opened, the filter 52 communicating with the outside air is communicated with the first exhaust switching valve 51 and the first container switching valve 56, and a pipeline from the filter communicating with the outside air to the first port 63 is communicated. Also, a flow passage from the first drainage bottle 79, the first discharge valve 81, and the first container discharge valve 84 is communicated with the second port 64 via the third pump 82. Subsequently, when the third pump 82 is turned ON for a predetermined time while giving a discharge time to discharge the liquid amount held in the first container 62 of the cell culture container 55, the liquid culture medium is sucked from the first container 62, and the liquid feeding is started, and liquid culture medium reaches the first drainage bottle 79. At this time, since the first port 63 is communicated with the outside air, pressure in the cell culture container 55 is adjusted to be a normal pressure. After a predetermined amount of the liquid has been discharged, the liquid feeding is terminated by stopping the third pump 82 and closing and turning OFF the opened valves.

When there is a plurality of cell culture containers, the first container switching valve 56 is closed by the operation, and the first container switching valve 58 in FIG. 5 is opened. Also, the first container discharge valve 84 is closed, and the first container discharge valve 85 in FIG. 5 is opened. After that, when the above operation is performed, the liquid culture medium is discharged from the first container 61 of the cell culture container 57.

When the liquid culture medium is added to the first container 62 (S09), the operation is performed according to the operation of the first container culture medium addition. When the culture medium switching valve 104, the first container switching valve 56, the second container switching valve 77, and the second exhaust switching valve 74 are turned ON at the initial state and these valves are opened, the culture medium preheating bottle 100 is communicated with the culture medium switching valve 104 and the first container switching valve 56, and a flow passage to the first port 63 is communicated. Also, the filter 52 communicated with outside air is communicated with the second exhaust switching valve 74 and the second container switching valve 77, and a pipeline from the filter connected to the outside air to the third port 65 is communicated. Subsequently, when the first pump 48 is turned ON for a predetermined time, the liquid culture medium starts to be fed from the preheating bottle 100, and the front end of the liquid culture medium reaches the first liquid level sensor 53. When a liquid level detection signal is output from the first liquid level sensor 53, the first pump 48 stops feeding the liquid. Next, when the fourth gas introducing valve 103 is opened, a liquid culture medium, of which the amount is determined, having the branch point 102 as the rear end and the first liquid level sensor 53 as the front end is created in the supply pipe 101. Subsequently, when the first pump 48 starts to feed the liquid, the liquid culture medium is fed from the first port 63 of the cell culture container 55 via the first container switching valve 56. At this time, since the third port 65 is communicated with the outside air, pressure in the cell culture container 55 is adjusted to be a normal pressure. After a predetermined amount of the liquid has been injected, the liquid feeding is terminated by stopping the first pump 48 and closing and turning OFF the opened valves.

When there is a plurality of cell culture containers, the liquid culture medium having an amount which can be distributed to the plurality of cell culture containers is previously held in the culture medium preheating bottle 100, and the first container switching valve 56 is closed by the above operation. Also, the first container switching valve 58 in FIG. 5 is opened, and the second container switching valve 77 is closed, and the second container switching valve 78 in FIG. 5 is opened. After that, when the above operation is performed, the same amount of the liquid culture medium is fed to the first container 62 of the cell culture container 57.

When the culture medium is discharged from the second container 61 in the cell culture container 55 (S10), the operation is performed according to the second container culture medium discharge operation in an operation time chart in FIG. 6. When the first container switching valve 56 and the first exhaust switching valve 51 are turned ON at the initial state, the second container discharge valve 88, and the second discharge valve 91, and these valves are opened, the filter 52 communicating with the outside air is communicated with the first exhaust switching valve 51 and the first container switching valve 56, and a pipeline from the filter communicating with the outside air to the first port 63 is communicated. Also, a flow passage between the second drainage bottle 86, the second discharge valve 88, and the second container discharge valve 91 is communicated with the third port 66 via the fourth pump 89. Subsequently, when the fourth pump 89 is turned ON for a predetermined time while giving a discharge time to discharge the liquid amount held in the second container 61 of the cell culture container 55, the liquid culture medium is sucked from the second container 61, and the liquid feeding is started, and liquid culture medium reaches the second drainage bottle 86. At this time, since the first port 63 is communicated with the outside air, pressure in the cell culture container 55 is adjusted to be a normal pressure. After a predetermined amount of the liquid has been discharged, the liquid feeding is terminated by stopping the fourth pump 89 and closing and turning OFF the opened valves.

When there is a plurality of cell culture containers, the first container switching valve 56 is closed by the operation, and the first container switching valve 58 in FIG. 5 is opened. Also, the second container discharge valve 91 is closed, and the second container discharge valve 92 in FIG. 5 is opened. After that, when the above operation is performed, the liquid culture medium is discharged from the second container 61 of the cell culture container 57.

When the liquid culture medium is added to the second container 61 (S11), the operation is performed according to the operation of the second container culture medium addition. When the culture medium switching valve 104, the first container switching valve 56, the second container switching valve 77, and the first exhaust switching valve 51 are turned ON at the initial state and these valves are opened, the culture medium preheating bottle 100 is communicated with the culture medium switching valve 104 and the second container switching valve 77, and a flow passage to the third port 65 is communicated. Also, the filter 52 communicated with outside air is communicated with the first exhaust switching valve 51 and the first container switching valve 56, and a pipeline from the filter connected to the outside air to the first port 63 is communicated. Subsequently, when the second pump 72 is turned ON for a predetermined time, the liquid culture medium starts to be fed from the preheating bottle 100, and the front end of the liquid culture medium reaches the second liquid level sensor 75. When a liquid level detection signal is output from the second liquid level sensor 75, the second pump 72 stops feeding the liquid. Next, when the fourth gas introducing valve 103 is opened, liquid culture medium, of which the amount is determined, having the branch point 102 as the rear end and the second liquid level sensor 75 as the front end is created in the supply pipe 102. Subsequently, when the second pump 72 starts to feed the liquid, the liquid culture medium is fed from the third port 65 of the cell culture container 55 via the second container switching valve 77. At this time, since the first port 63 is communicated with the outside air, pressure in the cell culture container 55 is adjusted to be a normal pressure. After a predetermined amount of the liquid has been injected, the liquid feeding is terminated by stopping the second pump 72 and closing and turning OFF the opened valves.

When there is a plurality of cell culture containers, the liquid culture medium having an amount which can be distributed to the plurality of cell culture containers is previously held in the culture medium preheating bottle 100, and the second container switching valve 77 is closed by the above operation. Also, the second container switching valve 78 in FIG. 5 is opened, and the first container switching valve 56 is closed, and the first container switching valve 58 in FIG. 5 is opened. After that, when the above operation is performed, the same amount of the liquid culture medium is fed to the second container 62 of the cell culture container 57.

Next, since the cell culture container 55 is filled with air, in order to fill it with $CO_2$ gas, an operation for filling $CO_2$ gas (S12) is performed according to the above.

When there is a plurality of cell culture containers, the first container switching valve 56 is closed by the above operation, and the first container switching valve 58 in FIG. 5 is opened. Also, the second container switching valve 77 is closed, and the second container switching valve 78 in FIG. 5 is opened. After that, when the above operation is performed, the cell culture container 57 is filled with $CO_2$ gas.

A specific example of a method for producing corneal epithelial cells by culturing corneal epithelial cells by using the cell culture apparatus and the liquid feeder according to the first embodiment and the result of the same will be described below.

<Structures of Cell Culture Apparatus and Liquid Feeder>

A thermostatic culture apparatus (TOYO ENGINEERING WORKS, LTD., model number TVHA60WA12A) is used as a thermostatic chamber, and the thermostatic culture apparatus is operated while setting an inner temperature to be 37° C. An electronic cooling/heating low temperature thermostatic device (TOYO ENGINEERING WORKS, LTD., model number THS030PA) is used as a refrigeration unit, and the refrigeration unit is operated while setting the inner temperature to be 4° C.

A pinch valve (fluid pressure 0.15 MPa, Takasago Electric, Inc., model number PSK-1615NC-9) is used as a solenoid valve. A silicon rubber tube (internal diameter 1/16 inch, outer diameter 1/8 inch, Saint-Gobain K.K, model number 3350) is used as a supply pipe corresponding to the solenoid valve. A tube pump (discharge/intake pressure+/− 0.1 MPa, Welco Co., Ltd., model number DSW2-S1AA-WP) is used as each pump, and a silicon rubber tube (internal diameter 1/16 inch, outer diameter 1/8 inch, Saint-Gobain K.K, model number 3355L) is used as a squeezing tube. Both of them are combined to be used. Since a roller of this product is removable from a motor of a body, a sterilization operation can be performed in a state where the silicon rubber tube with the length of 13 cm is wound around the roller. The flow rate of the pump is 0.15 mL/second based on the actual measurement in a case of DC 12 V input, and variation of the flow rate is in an amount corresponding to one percent at a maximum.

A closed system centrifugal tube (capacity 50 mL, Corning Incorporated, model number #11705) is used as a cell bottle and a culture medium preheating bottle. The product includes a container and a lid part which have been previously sterilized, a pipeline which is provided in the lid part and adjusts the air pressure, and a filter having a mesh size of 0.22 μm.

A closed system conical flask (capacity 1 L, Corning Incorporated, model number #11440) is employed as a culture medium bottle. The product includes a supply pipe (internal diameter 1/8 inch), a container, and a lid part which have been previously sterilized, a pipeline which is provided in the lid part and adjusts the air pressure, and a filter having a mesh size of 0.22 μm.

The Flexboy bag (capacity 1 L, Sartorius Japan K.K., model number #FFB103547) is used as a drainage bottle.

A gas washing bottle (capacity 500 mL, AS ONE Corporation, model number 6-129-02) is used as a humidifying bottle, and a filter (filter size 15×15 mm, AS ONE Corporation, model number 2-554-10) is used as a gas exchange unit. Both of them are combined to be used.

A Midisart 2000 (mesh size 0.22 μm, Sartorius Japan K.K., model number #17805-E) is used as a filter having contact with outside air of the gas introducing valve or the humidifying bottle.

A Tygon S-50-HL (internal diameter 1/16 inch, outer diameter 1/8 inch, Saint-Gobain K.K, model number 63010-390) is used as tubes other than the solenoid valve and the pump. The material of the Tygon is vinyl chloride. SMC coupling (Colder Products Company) series can be used as branches and joints of the tubes. Specifically, a Y Fitting (diameter of joint 1/16 inch, model number #HY291) is used as a two-branch joint, and a Straight Fitting (diameter of joint 1/16 inch, model number #HS291) is used as a straight line joint.

At the liquid level, a liquid level sensor (16 optical axes, KEYENCE CORPORATION., model number FU-95S) and a signal processing amplifier (KEYENCE CORPORATION., model number FS-N11MN) are connected to each other and used.

Regarding the structure of the liquid feeder, a process for feeding the cell suspension to a container 1 in the cell culture container will be described first. A supply pipe (internal diameter 3.7 mm) having a length of 10 cm is provided in the first cell bottle 34, and a silicon rubber tube (it is assumed that internal diameter be 1/16 inch and 1.58 mm. The same is applied below) having a length of 20 cm connects between the supply pipe and the branch point 38. A silicon rubber tube having a length of 15 cm connects between the branch point 38 and the suction port of the first pump 48, and a squeezing tube in the first pump 48 is connected with a silicon rubber tube having a length of 13 cm. The Tygon S-50-HL tube having a length of 80 cm connects between the discharge port of the first pump 48 and the multi-branch unit 54. The liquid level sensor 53 is placed so that a distance of 50 cm from the suction port of the first pump 48 becomes the center of a detected part by the liquid level sensor 53, and the liquid feeding amount of the cell suspension is 1.50 mL.

Figure 8:
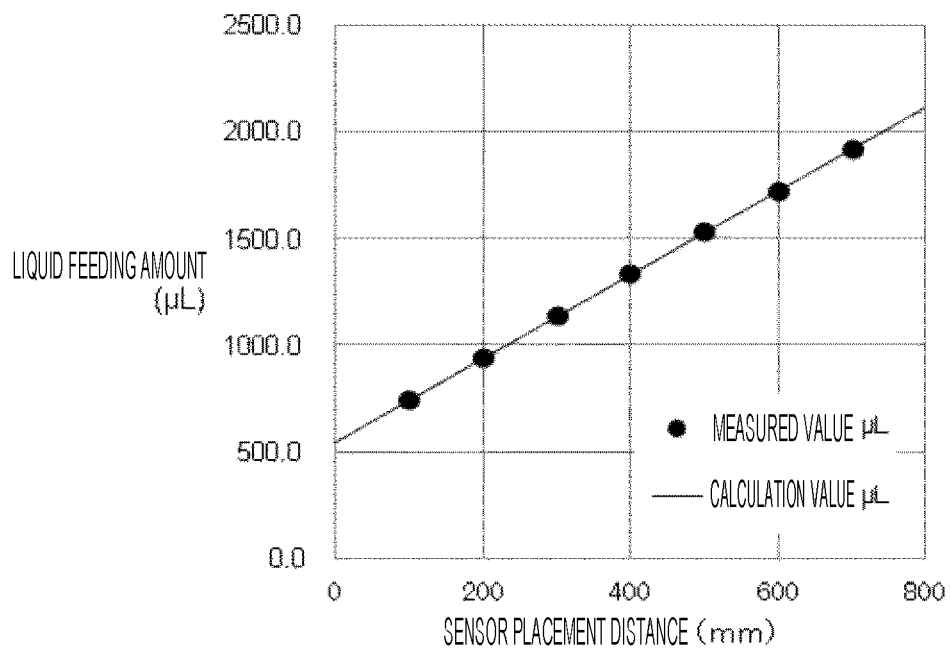
FIG. 8 is liquid feeding data of the liquid feeder according to the first embodiment.

The liquid feeding amount of the cell suspension is determined as follows. A volume in a tube between the supply pipe and the branch point 38 is the maximum liquid amount for returning to the liquid bottle at the time of introducing gas. The amount obtained based on the actual measurement has been 1.088 mL. The volume of the tube between the branch point 38 and a place where the liquid level sensor is placed corresponds to a target liquid feeding amount. FIG. 8 is liquid feeding amount data of the liquid feeder. A measured value is a liquid feeding amount (average value of ten times of measurements) of the liquid culture medium in a case where the liquid level sensor is extended by 10 cm in the silicon rubber tube having a length of 80 cm of the discharge pipe 50 between the first pump 48 and the multi-branch unit 54. A liquid amount held in the liquid bottle starts from 40 mL, and the measurement is continued even when the liquid amount is reduced relative to the number of measurement. A calculation value is a liquid feeding amount calculated according to volumes in the tubes including a tube having a length of 28 cm (13 cm+15 cm) from the branch point 38 to the pump discharge port and a tube having a length of 80 cm from the pump discharge port to the multi-branch unit.

As a result, regarding the measured value, the liquid feeding amount is correlated with the placing distance of the liquid level sensor, and standard deviation of each ten times of measurements is extremely small. Any of values obtained by dividing the standard deviation values by measured average values are of 0.3 to 0.5%. Also, the measured value coincides with the calculation value. The liquid feeding amount of 1.50 mL calculated back from the calculation value corresponds to 50.0 cm as the placing distance of the liquid level sensor. However, when a placing distance of the liquid level sensor optimized as having this as a guide is 50.0 cm, a measured value which is closest to the target value can be obtained at high reproducibility.

Similarly, a target value of feeding the cell suspension to a container 2 in the cell culture container has been 2 mL. However, when the optimized placing distance of the liquid level sensor is 74.0 cm, a measured value which is closest to the target value can be obtained at high reproducibility.

Regarding the liquid feeding time in this case, when a liquid feeding time of a first pump is set to be 30 seconds, the front end of the liquid reaches the liquid level sensor in an average of 20.4 seconds, and the pump is automatically stopped. After the gas introducing valve 39 is immediately opened, the liquid feeding time of the first pump to the culture container is set to be 60 seconds. At this time, all the liquid reaches the container 1 in about 32 seconds.

<Method for Producing Closed System Cell Culture Container>

The main body part 59, the lid part 60, and the first port 63 to the fourth port 66 included in the cell culture container illustrated in FIG. 5 are produced by injection molding while having polycarbonate as a material. A cell culture insert (6 well) having a model number of 353090 manufactured by Becton, Dickinson and Company is used as the first container. A temperature responsive culture surface is produced by electron-beam polymerizing the substance permeable film 9 with N-Isopropylacrylamide which is temperature responsive polymer monomer. A 35 mm cell culture surface treatment dish, of which model number is 430165, manufactured by Corning Incorporated is used as a second container.

The above components are assembled in a safety cabinet under a sterile condition, and the cell culture container is created. Next, after the cell culture container has been put in a sterilizing pack and sealed, the cell culture container is placed in an ethylene oxide gas sterilizer (model number EC-800, Sakura Seiki Co., Ltd.). Then, sterilization processing is performed according to a procedure for handling the device.

<Preparation for Corneal Epithelial Cells>

A method for culturing corneal epithelial cells will be described. On the day before a day when the corneal epithelial cells are cultured, NIH-3T3 cells, to which processing is performed with mitomycin C (10 µg/ml) for two hours at the temperature of 37° C., as feeder cells are suspended in the culture medium so as to be $2\times10^4/cm^2$. The NIH-3T3 cells are held in the second cell bottle 67. The corneal epithelial cells are collected from a limbus corneae of an eyeball of a rabbit purchased from Funakoshi Co., Ltd. by a usual method. Then, the corneal epithelial cells are suspended in the culture medium so as to be $4\times10^4/cm^2$ and held in the first cell bottle 34. A KCM culture medium including 5% of FBS is used as the culture medium including the above. As a spare culture medium, the KCM culture medium of 500 mL is held in the culture medium bottle 95, and they are placed in the refrigerator 33.

<Start to Culture Corneal Epithelial Cells>

The cell culture apparatus 31 is placed in the CPC, and the temperature in the apparatus is started to be held at a constant temperature of 37° C. Ten prepared cell culture containers are placed in the cell culture apparatus 31. After each solenoid valve has been connected to the cell culture container with the rubber tube, an automatic culture operation is started. A liquid feeding amount to an upper layer is 1.5 mL, and a liquid feeding amount to a lower layer is 2.0 mL. A liquid feeding amount of the culture medium is similar to this. In order to discharge all amount at the time of discharge, a discharge amount from the upper layer is 3 mL, and a discharge amount from the lower layer is 4 mL. The humidity of the $CO_2$ gas is controlled to be 95% H, and the air supply amount is the air supply flow rate of 0.1 L/minute. The amount of the injected air is more than the volume of 20 $cm^3$ in the cell culture container, and solenoid valve opening time is one minute (100 mL). The operation time chart above follows the outline of FIG. 6.

The culture medium is exchanged once a day on the fifth, the seventh, and the ninth to the 16th days from the culture start date. $CO_2$ gas is fed six times per day, that is, every four hours. In the microscope observation, first cells and second cells in each cell culture container are respectively obtained for 10 areas once per day from the fifth day, and the obtained cells are used as data for determining the cell growth state.

<Method for Recovering Corneal Epithelial Cell>

After the culture medium exchange operation on the 16 day of the culture, the cell culture is terminated, and the cell culture container is took out according to the above. The cell culture container is placed in the safety cabinet and left standing for 30 minutes at room temperature (about 25° C.). The first container is took out according to the above, and after that, the sheet shaped cells are peeled and recovered from a surface of a substance permeable film by using hydrophilic PVDF membrane (manufactured by Nihon Millipore K.K.) cut into a doughnut shape as a supporting film.

<Method of Control Experiment>

A cell culture insert companion plate including six wells (well internal diameter of 35 mm) in a plate of 2 inch×3 inch is used as a culture dish. The model number of the plate is 353502, and the plate is manufactured by Becton, Dickinson and Company. The same plate is used as an upper layer container. A $CO_2$ incubator, of which the model number is MCO19-AIC, manufactured by SANYO Electric Co., Ltd is used as temperature environment and $CO_2$ gas environment. The cell culture is performed at the temperature of 37° C., the humidity of 93% H, and the $CO_2$ concentration of 5%. Cells which are the same as the above are used.

The cell seeding and the culture medium exchange are performed by manual operation, and the liquid of which the amount is the same as the above is added by using a sterilized dispenser (PIPETMAN, Gilson, Inc., model number P5000). It is assumed that a frequency and interval of exchanges of the culture medium be the same as those in the above embodiments. Control of $CO_2$ gas is similarly set through the culture. At the time of exchanging the culture medium, the companion plate is placed on a hotplate with the temperature of 37° C., and the operation is performed so as to maintain the temperature.

<Results of Culture Experiment>

All the ten sheet shaped cells that are the corneal epithelial cells produced in the cell culture container of the present embodiment have the same size and thickness, and the cells can be stably peeled and recovered. When microscope images in a growing process are compared with each other, the growth of ten cells has no significant differences. On the other hand, the shapes of the produced cells are similar to those of the culture cells recovered by performing the control experiment.

Slices of the corneal epithelial cells are created, and the culturing cells are observed by hematoxylin-eosin stain and immune tissue dyeing. In both groups of the present embodiment and the control experiment, the CK protein family expressed in the epithelial cells is expressed in all the cells.

CK3 expressed in the differentiated corneal epithelial cells expresses in cells other than a base layer. Claudin 1 which is closed binding protein necessary for a barrier function of the epithelial cells is expressed in an outermost layer, and Claudin 1 in two groups has no significant differences. Therefore, the present apparatus can be considered to have the same liquid feeding accuracy as that of the dispenser used in the manual operation.

The first problem is avoided by the liquid feeder according to the first embodiment. The first problem is an effect of the liquid level position relative to the liquid amount change in the liquid bottle which is the liquid feeding source. Also, the second problem that is an effect of the liquid level position of the returned liquid is avoided. This is because, even when the liquid level position is at any positions in the liquid bottle of the liquid feeding source, the position of the liquid level moves in the liquid feeding pipe by feeding the liquid by the pump and finally stops at the position of the liquid level sensor and comes at a known position. The liquid feeding amount is equal to a volume managed by a product of a cross-sectional area of the pipe and a distance of the liquid level sensor 21 which is placed at a calculated distance from the branch point 9 according to the target liquid feeding amount, and the liquid has the rear end positioned at the branch point and the front end positioned at the liquid level sensor at the time of introducing the gas.

In addition, the third problem that is the change of the pump flow rate due to the effect by the length of the rubber tube and the like can be avoided. The reason is as follows. The liquid feeding amount is not defined based on the time control calculated from the pump flow rate. Also, the liquid feeding amount is equal to the volume managed by the product of the cross-sectional area of the pipe and the distance of the liquid level sensor 21 which is placed at a calculated distance from the branch point 9 according to the target liquid feeding amount, and the liquid has the rear end positioned at the branch point and the front end positioned at the liquid level sensor at the time of introducing the gas.

Therefore, according to the cell culture apparatus including the liquid feeder, after the liquid such as the liquid culture medium or the cell suspension passed through the pipeline, and the gas passed through the pipeline in the direction of the culture container. Accordingly, since the liquid culture medium in the pipeline is evacuated and the gas passes to the direction of the liquid bottle for holding the liquid culture medium and the like, the liquid such as the liquid culture medium is not maintained in the pipeline does not close the pipeline. Also, a liquid feeding error relative to the target liquid feeding amount is small, and variation of repeated liquid feeding amounts is small. Therefore, the liquid feeding amounts relative to the plurality of containers can be fixed. Accordingly, since a fixed amount of the cell suspension can be added to each of the culture containers, reproducibility of the cell culture is improved.

Second Embodiment

A liquid feeder according to the present embodiment and a cell culture apparatus for using the same solve the problem of the present invention. In addition, the liquid feeder and the cell culture apparatus can be applied in a case where the liquid of any target amounts is fed.

The important point of the solution is to include the liquid bottle 2 for holding the liquid, the supply pipe 5 for conducting the liquid, the gas introducing valve 10, the pump 6, and the liquid level detection unit 21. Also, the point includes to control the liquid feeding amount enough for the target liquid feeding amount while having time when the liquid level has reached the liquid level detection unit as a reference.

Figure 9:
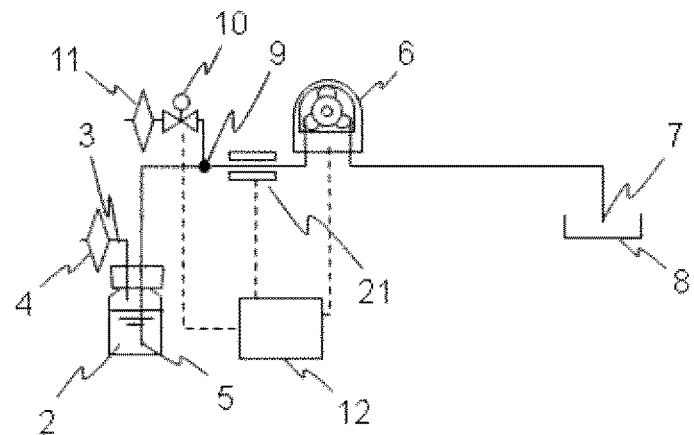
FIG. 9 is a block diagram of a liquid feeder according to a second embodiment.

FIG. 9 is a diagram of a structure of a liquid feeder 110 according to a second embodiment, and the basic structure is the same as those of the conventional apparatus and the first embodiment for using the drop of the liquid. A liquid bottle 2, an air pressure adjusting pipeline 3, a filter 4, a supply pipe 5, a pump 6, a discharge pipe 7, a receptor 8, a branch point 9, a gas introducing valve 10, a filter to introduce gas 11, and a controller 12 are the same as those in the first embodiment.

A liquid level sensor 21 detects whether the liquid exists in the discharge pipe 7. As illustrated in FIG. 9, a point that the liquid level sensor 21 is provided between the branch point 9 and the pump 6 is different from the first embodiment.

The gas feeder 110 determines the amount of the liquid and feeds the liquid as follows. It is assumed that a flow rate of the pump 6 be Q. When the pump 6 is operated after the gas introducing valve 10 is closed, the pump 6 feeds the gas in the supply pipe 5, and the liquid in the liquid bottle 2 connected to the gas passes through the supply pipe 5. Then, the liquid feeding is started. An operation time of the pump 6 is not especially determined. When the liquid passes through the branch point 9 and the liquid level reaches the position where the liquid level sensor 21 is provided, the pump 6 is stopped. Since the pipe is closed by an internal structure of the pump 6, the liquid does not move. In a case where it is assumed that the target liquid feeding amount be A and a volume in the pipe from the position of the branch point 9 to the position where the liquid level sensor 21 is placed be A1, when it is assumed that the amount to be adjusted relative to the target liquid feeding amount be A2, A2 is obtained by A-A1. Next, an operation time of the pump 6 is controlled so that the pipe is filled with the liquid having the adjusting amount A2 which is enough for the target liquid feeding amount. The operation time can be obtained by an adjusting amount A2/Q (pump flow rate).

Next, when the gas introducing valve 10 is opened, the gas is introduced through the filter 11, and the liquid in the supply pipe 5 on the side of the liquid bottle from the position of the branch point 9 returns to the liquid bottle 2 by drop energy of the liquid. The liquid on the side of the pump 6 from the branch point 9 is maintained in a stop state by the internal structure of the pump 6. The amount of the liquid on the side of the pump is the liquid feeding amount. Next, when the pump 6 is operated for a predetermined time, the gas is sequentially introduced from the filter 11, and the liquid moves in the discharge pipe 7. When the front end of the liquid reaches the receptor 8, and addition of the liquid is started, and the rear end of the liquid reaches the receptor 8, the pump 6 is stopped.

Figure 10:
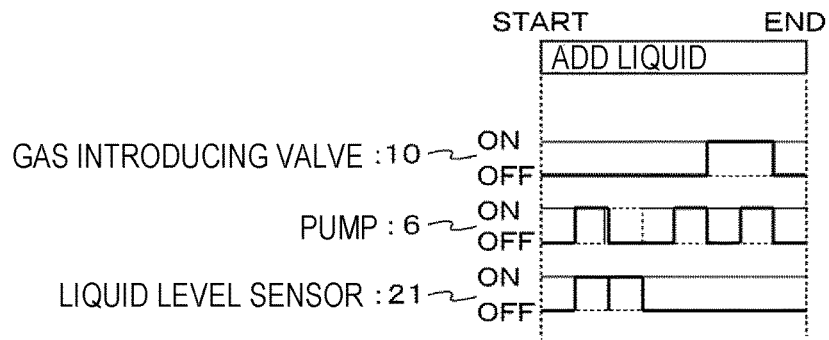
FIG. 10 is a control flowchart of the liquid feeder according to the second embodiment.

FIG. 10 is a control flowchart of the second embodiment. First, the pump 6 is operated at the time of "START", and the liquid feeding is started. When the front end of the liquid reaches the liquid level sensor 21, the operation of the pump 6 is immediately stopped in response to a signal from the liquid level sensor. Next, the pump 6 is started to feed the liquid by giving a liquid feeding time corresponding to the adjusting amount which is enough for the target liquid feeding amount (in FIG. 10, a line looked like double lines on the right side of ON-OFF of the pump 6 indicates that the pump is turned ON for a short time to adjust the amount of the liquid). After the pump is stopped, the gas introducing valve 10 is opened. The pump 6 is operated for a period which is set to be longer than time until the rear end of the liquid reaches the receptor 8, and the gas introducing valve 10 is closed after arbitrary time.

It is preferable that the position where the liquid level sensor 21 is placed be a position having a managed distance from the branch point 9. For example, the position may be between the pump 6 and the receptor 7, and in addition, may be between the branch point 9 and the liquid bottle 2. That is, when the volume in the pipe is estimated based on a distance between the branch point 9 and the place where the liquid level sensor 21 is placed has been known, the liquid feeder can be applied to any liquid feeding amounts. The adjusting amount is derived from A-A1 to obtain A2. Different from FIG. 9, when the liquid level sensor 21 is closer to the liquid bottle than the branch point 9, A1 is a negative value. However, the adjusting amount can be applied by the same operation method as above.

In a case where the liquid feeder 110 according to the second embodiment is used, the liquid level can be managed to be the position of the liquid level sensor 21 by feeding the liquid by the pump even when the liquid level position in the liquid bottle 2 of the liquid feeding source is positioned at any positions in the supply pipe 5. According to this, an effect of the change of the liquid level due to the liquid amount in the liquid bottle can be avoided. At this time, the liquid feeding amount enough for the target liquid feeding amount is estimated based on the pump flow rate while having the position of the liquid level as a reference, and the amount is controlled as a pump operation time. Accordingly, the liquid feeding amount can be controlled to be constant. In this case, liquid feeding variation of the pump is added to the liquid feeding amount. However, this does not damage the accuracy and reproducibility of the liquid feeding. In addition, in the first embodiment, high accuracy of the liquid feeding is obtained by fixing a position of a liquid level detection unit according to the target liquid feeding amount and performing the operation. However, the present embodiment can be applied when any amounts of liquid are fed, and versatility is improved. Also, the maximum liquid feeding amount of a single time of processing in the first embodiment is the volume in the pipe from the branch point to the receptor at the time of introducing gas. However, in the present embodiment, the amount held in the liquid bottle is the maximum, and the liquid feeding amount of a single time of processing can be basically set without limitation.

According to the cell culture apparatus including the liquid feeder 110 according to the second embodiment, the target liquid feeding amount can be changed without changing the position of the liquid level sensor. For example, depending on the cell culture state, the cell culture apparatus can cope with a case where an adding amount of the culture medium at the time of exchanging the culture medium is increased/decreased during automatic culturing.

Third Embodiment

According to a liquid feeder according to the present embodiment and a cell culture apparatus for using the same, the problem of the present invention is solved. In addition, an effect of physical damage to cells to be fed can be reduced while the liquid of an optional amount is fed.

The important point of the solution is to include the liquid bottle for holding the liquid, the liquid feeding pipe for conducting the liquid, the gas introducing valve, the liquid level detection unit, a pressurizing unit for pressurizing the liquid bottle, and a gas introducing unit to the liquid bottle. Also, the point includes to control the liquid feeding amount enough for the target liquid feeding amount while having time when the liquid level has reached the liquid level detection unit as a reference and to provide a unit for feeding the liquid of which the amount is determined.

Figure 11:
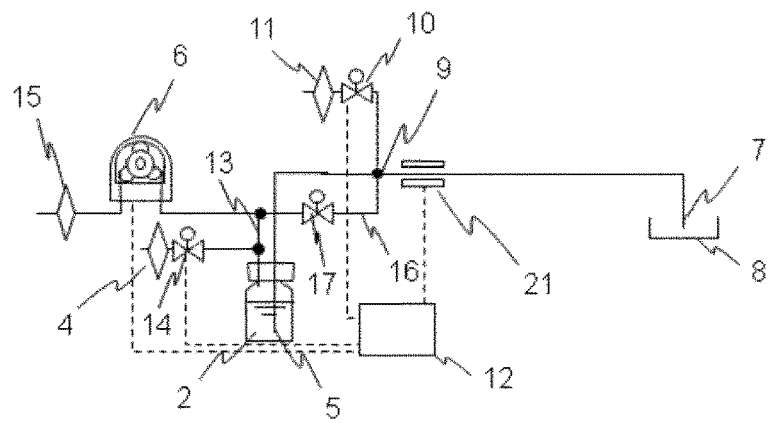
FIG. 11 is a block diagram of a liquid feeder according to a third embodiment.

FIG. 11 is a diagram of a structure of a liquid feeder 111 according to a third embodiment. The basic structure is the same as those of the conventional apparatus and the second embodiment for using a drop of the liquid, and a method for determining a target liquid feeding amount is the same as that of the second embodiment. On the other hand, a pump which is a liquid feeding unit is not provided in a liquid feeding pipe between a liquid bottle and a receptor and is used as a unit for pressurizing the liquid in the liquid bottle. The present embodiment is characterized by this point. That is, except for the pump 6, the structures of a liquid bottle 2, a supply pipe 5, a discharge pipe 7, a receptor 8, a branch point 9, a gas introducing valve 10, a filter to introduce gas 11, a controller 12, and a liquid level sensor 21 are the same as those in FIG. 9 representing the second embodiment. A suction port of the pump 6 is connected to a filter 15 communicating with outside air, and a discharge port is branched into two. One of them is connected to an air supply valve 17, and another one is connected to an air pressure adjusting pipeline 13 in the liquid bottle. Also, a branch is provided in the air pressure adjusting pipeline 13 and connected to the filter 4 communicating with the outside air via a bottle pressure control valve 14. The supply pipe 5 having contact with the liquid in the liquid bottle is connected to the gas introducing valve 10 and an air supply pipe 16 extended from the air supply valve 17 at the branch point 9.

Figure 12:
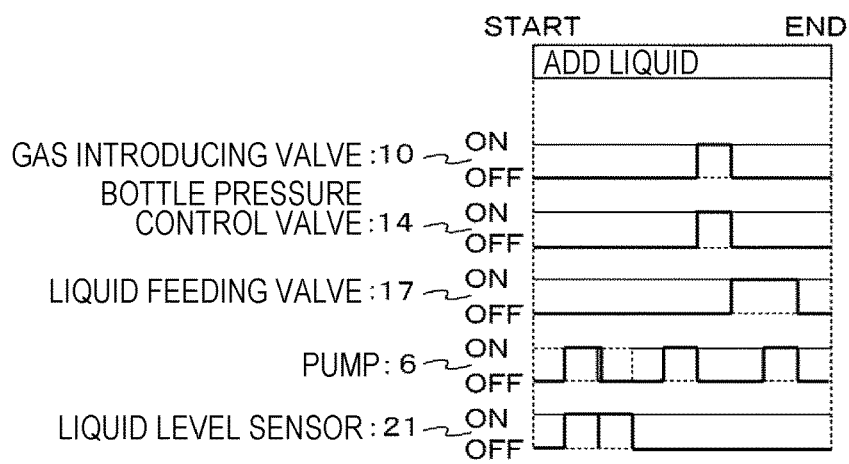
FIG. 12 is a control flowchart of the liquid feeder according to the third embodiment.

The gas feeder 111 determines the amount of the liquid and feeds the liquid as follows. FIG. 12 is a control flowchart of the third embodiment. First, the pump 6 is operated at the time of "START", and the liquid feeding is started. When the front end of the liquid reaches the liquid level sensor 21, the operation of the pump 6 is immediately stopped in response to a signal from the liquid level sensor. Next, a liquid feeding time corresponding to an adjusting amount which is enough for the target liquid feeding amount is given to the pump 6, and the pump 6 starts to feed the liquid. When the gas introducing valve 10 and the bottle pressure control valve 14 are opened after the pump has been stopped, gas is introduced from the branch point 9, and the liquid returns to the liquid bottle 2 due to a drop. Next, the gas introducing valve 10 and the bottle pressure control valve 14 are closed, and the liquid feeding valve 17 is opened. At this time, the discharge port of the pump 6 is opened relative to the liquid in the pipe, of which an amount is the target liquid feeding amount having the branch point 9 as a rear end, via the liquid feeding valve 17. After that, the pump 6 is operated for a period which is set to be longer than time until the rear end of the liquid reaches the receptor 8, and the liquid feeding valve 17 is closed after arbitrary time.

When the liquid feeder 111 according to the third embodiment is used, the liquid having an optional liquid feeding amount can be fed with constant reproducibility without effected by the liquid level position in the liquid bottle 2 which is the liquid feeding source based on the effect of the second embodiment. In addition, an effect of physical damage on the cells to be fed can be reduced. The reason is as follows. In a liquid feeding method for using a general pump such as a roller pump, a diaphragm pump, and a gear pump as the liquid feeding unit, a closed part and an opened part are included as the liquid feeding structure and directly provide pressure to the cells for passing therethrough. Therefore, an effect on the cell culture is concerned. In the present embodiment, since the pump is used as a unit to pressurize the liquid in the liquid bottle, the cells do not pass through the pump. Therefore, an effect to reduce the influence of the physical damage on the cells can be obtained. In the description, the pump is used as the liquid feeding unit and the pressurizing unit. However, when a unit which is capable of pressurizing the liquid is used, and the unit is not limited to this. For example, a syringe pump including a combination of a piston and a cylinder and a method for holding inert gas with high pressure and controlling a pressurizing force and pressurizing time to the liquid have no closed part and opened part as the liquid feeding structure. Therefore, the method has small effect on the cell culture.

Fourth Embodiment

According to a liquid feeder according to the present embodiment and a cell culture apparatus for using the same, the problem of the present invention can be solved by a following method without using the above-mentioned liquid level detection unit.

The important point of the solution is to include a liquid bottle for holding the liquid, a liquid feeding pipe for conducting the liquid, a gas introducing valve, a pump, and an outside air introducing unit and to apply the outside air pressure from the liquid feeding pipe to the liquid bottle.

Figure 13:
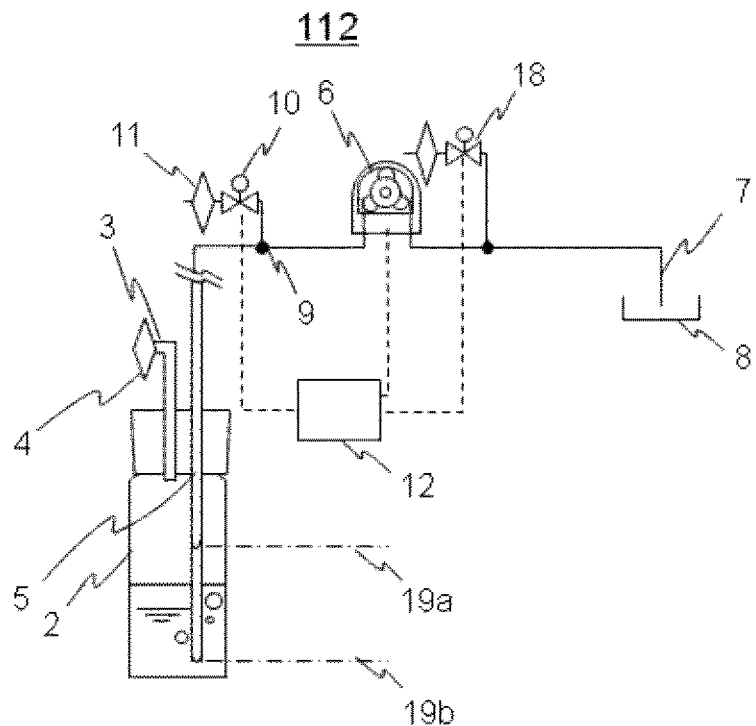
FIG. 13 is a block diagram of a liquid feeder according to a fourth embodiment.

FIG. 13 is a diagram of a structure of a liquid feeder 112 according to a fourth embodiment. The basic structure is the same as that of the conventional apparatus for using a drop of the liquid, and a method for determining a target liquid feeding amount is time control based on a pump flow rate and is the same as that of the conventional method.

On the other hand, the pump is operated as the outside air introducing unit and makes the outside air pressure apply from the liquid feeding pipe to the liquid bottle in a liquid feeding direction opposite to a normal direction. The present embodiment is characterized by this point. That is, structures of a liquid bottle 2, an air pressure adjusting pipeline 3, a filter 4, a supply pipe 5, a pump 6, a discharge pipe 7, a receptor 8, a branch point 9, a gas introducing valve 10, a filter to introduce gas 11, and a controller 12 are the same as those of the conventional example in FIG. 3. One side of an outside air introducing valve 18 is connected to the filter communicating with outside air, and another side is connected to the middle of the pipeline of the discharge pipe 7 between the pump 6 and the receptor. A structure of the liquid bottle 2 is illustrated in an enlarged diagram, and a liquid level position 19a according to held liquid amount is illustrated as a liquid level position in the supply pipe 5. As described in a section of "Technical Problem", the liquid level position 19a is changed according to a case where the liquid is returned due to the drop and a case where the liquid amount is reduced by feeding the liquid, and therefore, the liquid level position 19a cannot be uniquely determined. A liquid level position 19b indicates an opening position of the supply pipe 5 and is controlled according to the third embodiment.

Figure 14:
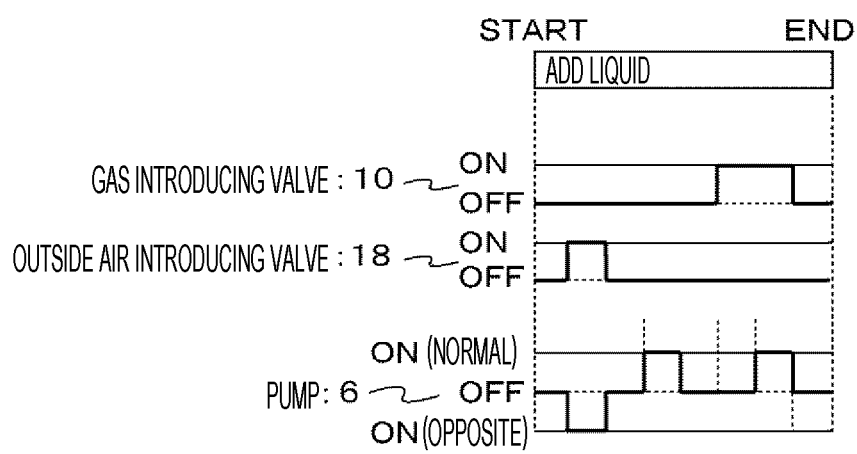
FIG. 14 is a control flowchart of the liquid feeder according to the fourth embodiment.

The liquid feeder 112 determines the amount of the liquid and feeds the liquid as follows. FIG. 14 is a control flowchart of the fourth embodiment. When the outside air introducing valve 18 is turned ON and opened at the time of "START", the outside air introducing valve 18, the pump 6, and the supply pipe 5 are communicated with each other. Next, the pump 6 feeds the gas in the direction opposite to the liquid feeding direction. The air supply amount is experimentally obtained so that the liquid level at any positions in the supply pipe 5 is pressed down and the outside air is released into the liquid in the liquid bottle. Next, the outside air introducing valve 18 is closed, and the pump 6 feeds the liquid in the direction opposite to the normal liquid feeding direction. After that, a method for using the liquid feeder is the same as the conventional method and the method for using the liquid feeder 1 described with reference to FIG. 3.

In a liquid feeding method for using a general pump such as a roller pump, a diaphragm pump, and a gear pump as the liquid feeding unit, when energizing polarities to positive and negative electrodes of a motor is changed, the liquid feeding direction can be optionally changed to the standard direction and the opposite direction. In the present embodiment, the liquid level is controlled by feeding vapor phase in a direction opposite to the normal liquid feeding direction. Also, even when the outside air introducing unit other than the pump is used, the unit can be applied to the present embodiment. For example, as the structures in FIG. 5 similar to those in FIG. 13, the filter 52 and the second exhaust switching valve 51 have the same function as that of the outside air introducing valve 18. Also, a gas supply line including the first gas switching valve 43, the humidifying bottle 44, the filter 45, the pressure control valve 46, and the gas cylinder 47 can be used as the outside air introducing unit when the gas feeding direction is controlled to be the direction to the liquid bottle.

The first problem is avoided by the liquid feeder 112 according to the fourth embodiment. The first problem is an effect of the liquid level position relative to the liquid amount change in the liquid bottle which is the liquid feeding source. Also, the second problem that is an effect of the liquid level position of the returned liquid is avoided. This is because, even when the liquid level position is at any positions in the liquid bottle which is the liquid feeding source, the outside air introducing unit make the outside air pressure apply from the liquid feeding pipe to the liquid bottle, and accordingly, the liquid level position stops at an opening of the liquid feeding pipe and comes at a known position. In addition, extra outside air and pressure pass through the liquid in the liquid bottle and move from the air pressure adjusting pipeline 3 through the filter 4 and are released to outside air, and inside the liquid bottle can be maintained to have a normal pressure. Since the liquid feeding amount is controlled by a method same as the conventional method, the change of the pump flow rate due to the effect of the length of the rubber tube which is the third problem cannot be avoided. However, the above two problems have larger effect on a factor of the variation of the flow rate, and an effect can be obtained in which the liquid can be fed while the flow rate change is maintained within the flow rate variation of the pump itself.

Fifth Embodiment

According to a liquid feeder according to the present embodiment and a cell culture apparatus for using the same, the problem of the present invention can be solved while confirming a liquid feeding amount by using the following method in addition to the liquid level detection unit.

The important point of the solution is to include a liquid bottle for holding the liquid, a liquid feeding pipe for conducting the liquid, a gas introducing valve, a pump, and a weight measuring unit of the liquid bottle.

Figure 15:
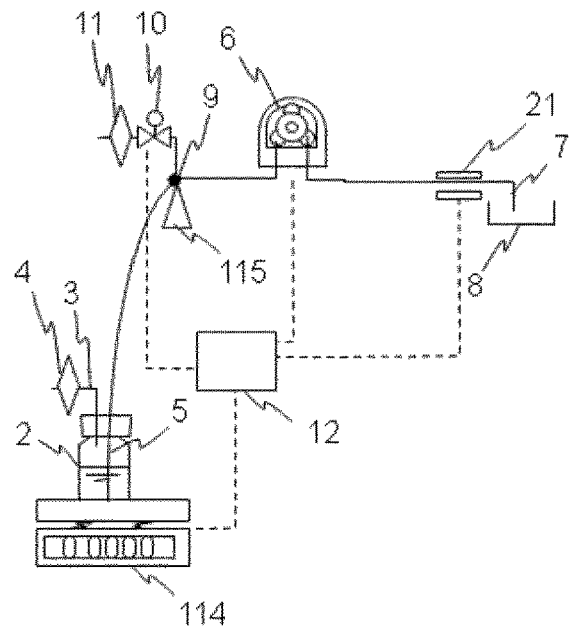
FIG. 15 is a block diagram of a liquid feeder according to a fifth embodiment.

FIG. 15 is a diagram of a structure of a liquid feeder 113 according to a fifth embodiment. The basic structure is the same as that of the first embodiment. However, a method for detecting a weight change value of the liquid bottle is used as a method for confirming the liquid feeding amount. That is, structures of a liquid bottle 2, an air pressure adjusting pipeline 3, a filter 4, a supply pipe 5, a pump 6, a discharge pipe 7, a receptor 8, a branch point 9, a gas introducing valve 10, a filter to introduce gas 11, a controller 12, and a liquid level sensor 21 are the same as those of the conventional example in FIG. 3. A weight sensor 114 measures a weight of a group of the liquid bottle 2 holding the liquid, the air pressure adjusting pipeline 3, and the filter 4. A fixing jig 115 fixes a branch part 9. When a pipe material having high flexibility such as a rubber tube is used for the supply pipe 5, it is preferable that components connected to the other side of the branch point 9 do not interfere with the weight measurement.

Figure 16:
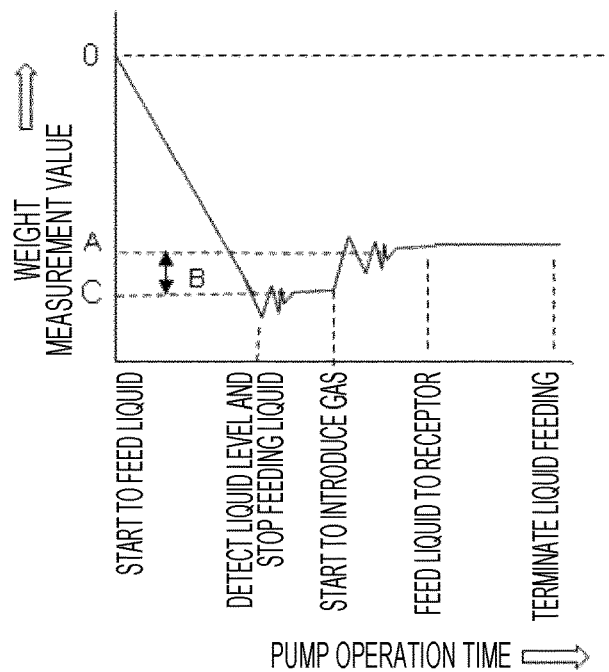
FIG. 16 is a diagram of weight measurement data of the liquid feeder according to the fifth embodiment.

The liquid feeder 113 feeds the liquid and confirms the liquid feeding amount as follows. In FIG. 16, the horizontal axis indicates a control order of the fifth embodiment, and the vertical axis indicates a weight measurement value obtained by the weight sensor corresponding to that.

The control flowchart follows the control flowchart of the liquid feeder according to the first embodiment illustrated in FIG. 2. The pump 6 starts to feed the liquid. Next, when the liquid level sensor 21 detects the liquid level, the liquid feeding is stopped, and a total liquid amount weight C can be obtained.

The total liquid amount weight C is obtained by adding a target weight A obtained based on a density and a weight (return amount) B to the target liquid amount. The weight B is obtained based on a density of the liquid in a case where a volume of a pipe corresponding to the liquid level of the liquid in the liquid bottle 2 from the branch point 9 is filled with the liquid.

Next, when the gas introducing valve 10 is opened, the gas is introduced through the filter 11, and the liquid in the supply pipe 5 on the side of the liquid bottle from the position of the branch point 9 (return amount B) returns to the liquid bottle 2 by drop energy of the liquid. At this time, the weight measurement value indicates a value smaller than C, and a weight indicating value is the target weight A. A difference between the values A and C is the returned weight B. The liquid on the side of the pump 6 from the branch point 9 is maintained in a stop state by the internal structure of the pump 6.

Next, when the pump 6 is operated for a predetermined time, the gas is sequentially introduced from the filter 11, and the liquid moves in the discharge pipe 7. When the front end of the liquid reaches the receptor 8, and addition of the liquid is started, and the rear end of the liquid reaches the receptor 8, the pump 6 is stopped. In this period, the weight measurement value does not change. When the liquid is repeatedly fed, a weight which is sequentially reduced can be treated as the liquid feeding weight by performing the operation.

When the liquid feeder is combined with the cell culture apparatus for using the liquid feeder according to the first embodiment illustrated in FIG. 5, this can be used to determine and confirm the liquid feeding amount of the cell suspension at the time of seeding the cells. In a general cell culture process, the skill level of an operator and an operation performing record secure the performance of the dispensation process. When the present embodiment is used, a record of a single dispensation operation is made by recording that liquid having the target weight is reduced from the weight of the cell bottle to be the liquid feeding source, and this secures the reliable performance results of the cell culture process.

Also, when the first drainage bottle 79 and the second drainage bottle 86 of the cell culture apparatus illustrated in FIG. 5 include the same weight sensors 114, a record of a single liquid feeding operation from the culture container is made by recording that the liquid having the target weight is increased from the weight of the drainage bottle to be a discharge source, and this secures the reliable performance results of the culture medium exchange process.

In this way, when operation information obtained from an automatic apparatus is arranged, performance results of the liquid feeding and discharge can be secured with high reliability. The operation information includes a record of time when all the pumps are operated, a record of a voltage applied to the pump, and a record of operation time of the liquid level sensor.

INDUSTRIAL APPLICABILITY

The present invention is useful as a cell culture apparatus for culturing cells and a liquid feeder.

REFERENCE SIGNS LIST 1 liquid feeder
2 liquid bottle
3 air pressure adjusting pipeline
4 filter
5 supply pipe
6 pump
7 discharge pipe
8 receptor
9 branch point
10 gas introducing valve
11 filter
12 controller
20 liquid feeder according to the first embodiment
21 liquid level sensor
22 liquid level sensor body
23 light source
24 light receiving window
25 signal line
26 installation tool
27 installation base
28 pipe fixing unit
29 detection light
30 reflection light
31 automatic cell culture apparatus
32 thermostatic chamber
33 refrigerator
34 first cell bottle
35 air pressure adjusting pipeline
36 filter
37 supply pipe
38 branch point
39 first gas introducing valve
40 first cell switching valve
41 filter
42 common pipe
43 first gas switching valve
44 humidifying bottle
45 filter
46 pressure control valve
47 gas cylinder
48 first pump
49 second gas switching valve
50 discharge pipe
51 first exhaust switching valve
52 filter
53 first liquid level sensor
54 multi-branch unit
55 first culture container
56 first container switching valve
57 second culture container
58 first container switching valve
59 main body part 60 lid part
61 second container
62 first container
63 first port
64 second port
65 third port
66 fourth port
67 second cell bottle
68 supply pipe
69 branch point
70 second gas introducing valve
71 second cell switching valve
72 second pump
73 discharge pipe
74 second exhaust switching valve
75 second liquid level sensor
76 multi-branch unit
77, 78 second container switching valve
79 first drainage bottle
80 drain pipe
81 first discharge valve
82 third pump
83 multi-branch unit
84,85 first container discharge valve
86 second drainage bottle
87 drain pipe
88 second discharge valve
89 fourth pump
90 multi-branch unit
91,92 second container discharge valve
95 culture medium bottle
96 supply pipe
97 branch point
98 a third gas introducing valve
99 fifth pump
96 supply pipe
100 culture medium preheating bottle
101 supply pipe
102 branch point
103 fourth gas introducing valve
104 culture medium switching valve
110 liquid feeder according to the second embodiment
111 liquid feeder according to the third embodiment
13 air pressure adjusting pipeline
14 bottle pressure control valve
15 filter
16 air supply pipe
17 air supply valve
112 liquid feeder according to the fourth embodiment
18 outside air introducing valve
19a liquid level position of the conventional method
19b controlled liquid level position
113 liquid feeder according to the fifth embodiment
114 weight sensor
115 fixing jig

The invention claimed is:

1. A liquid delivery device comprising:
   a liquid feeding pipe configured to include a liquid introduction port and a liquid discharge port;
   a housing container configured to hold a liquid culture medium in communication with the liquid introduction port;
   a pump disposed between the liquid introduction port and the liquid discharge port and configured to feed the liquid culture medium in the housing container from the liquid introduction port through the liquid feeding pipe to the liquid discharge port;
   a gas introduction valve connected to a branch point on the liquid feeding pipe between the liquid introduction port and the pump and configured to introduce gas into the liquid feeding pipe;
   a liquid sensor configured to detect an advancing liquid level of the liquid culture medium in the liquid feeding pipe; and
   a controller programmed to control the pump and the gas introduction valve based on a signal from the liquid sensor,
   wherein the branch point is disposed on an upstream side of the liquid feeding pipe from the pump,
   wherein the liquid sensor is provided on a downstream side of the liquid feeding pipe from the branch point, and
   wherein the controller is further programmed to:
   cause the pump to feed the liquid culture medium from the liquid introduction port towards the liquid sensor,
   open the gas introduction valve to introduce the gas into the liquid feeding pipe which causes the liquid culture medium in the liquid feeding pipe upstream from the branch point to return to the housing container, and
   control the pump to feed the liquid culture medium in the liquid feeding pipe downstream from the branch point to the liquid discharge port.

2. The liquid delivery device according to claim 1, wherein the liquid sensor is provided on the liquid feeding pipe downstream from the pump, and the liquid sensor is arranged at a position on the liquid feeding pipe where an amount of the liquid culture medium in the liquid feeding pipe between the liquid level sensor and the branch point is a predetermined liquid feeding amount, and
wherein the controller is further programmed to, when the liquid sensor has detected the advancing liquid level of the liquid culture medium, stop the feeding by the pump.

3. The liquid delivery device according to claim 2, further comprising:
   a weight sensor configured to measure a weight of the housing container, and
   wherein the controller is further programmed to determine an amount of the liquid culture medium discharged from the liquid discharge port based on a difference between the weight of the housing container when the pump has been stopped and the weight of the housing container when the gas introduction valve has been opened.

4. The liquid delivery device according to claim 1, wherein the liquid sensor is provided on the liquid feeding pipe upstream from the pump, and
wherein the controller is further programmed to control the pump to feed a predetermined liquid feeding amount based on a time when the liquid sensor has detected the advancing liquid level of the liquid.

5. The liquid delivery device according to claim 1, wherein
the branch point is arranged above the housing container relative to a gravity direction.

6. The liquid delivery device according to claim 1, wherein the liquid sensor includes:
   a plurality of light sources arranged along the liquid feeding pipe, and
   a plurality of light receiving windows arranged at a position corresponding to the plurality of light sources.

7. The liquid delivery device according to claim 1, wherein the liquid sensor includes a first sensor and a second sensor placed on the downstream side of the first sensor, and the controller is further programmed to stop the pump when the signal from at least one of the first and second sensors is erroneous.

8. The liquid delivery device according to claim 1, further comprising:

a filter configured to remove contaminants from the gas prior to the gas introduction valve.

9. A cell culture device comprising:

the liquid delivery device according to claim 1, a thermostatic chamber storing a culture container in communication with the liquid discharge port; and a low-temperature storage container, wherein the housing container is stored in the low-temperature storage container and held in a low temperature state, and wherein the culture container, the pump, the gas introduction valve, the liquid sensor, and the liquid discharge port are stored in the thermostatic chamber and controlled at a constant temperature.

10. The cell culture device according to claim 9, wherein the liquid feeder prevents a liquid feeding malfunction of the liquid culture medium including the cells and the culture medium.

11. A liquid delivery device comprising:

a liquid feeding pipe configured to include a liquid introduction port and a liquid discharge port;

a housing container configured to hold a liquid culture medium in communication with the liquid introduction port;

a pump disposed between the liquid introduction port and the liquid discharge port and configured to feed the liquid culture medium in the housing container from the liquid introduction port through the liquid feeding pipe to the liquid discharge port;

a gas introduction valve connected to a first branch point on the liquid feeding pipe between the liquid introduction port and the pump and configured to introduce gas into the liquid feeding pipe;

a liquid sensor configured to detect an advancing liquid level of the liquid culture medium in the liquid feeding pipe;

an outside air introduction valve connected to a second branch point on the liquid feeding pipe between the pump and the liquid discharge port and configured to introduce outside air into the liquid feeding pipe; and a controller programmed to control the pump, the gas introduction valve, and the outside air introduction valve, wherein the controller is further programmed to:

open the outside air introduction valve to introduce the outside air into the liquid feeding pipe and cause the pump to feed the outside air into the housing container, close the outside air introduction valve and cause the pump to feed the liquid culture medium from the liquid introduction port towards the liquid sensor, open the gas introduction valve to introduce the gas into the liquid feeding pipe which causes the liquid culture medium in the liquid feeding pipe upstream from the branch point to return to the housing container, and control the pump to feed the liquid culture medium in the liquid feeding pipe downstream from the branch point to the liquid discharge port wherein the outside air is fed into the housing container in a direction opposite to the liquid culture medium fed into the liquid feeding pipe at the liquid introduction port.

12. A liquid delivery device comprising:

a liquid feeding pipe configured to include a liquid introduction port and a liquid discharge port;

a housing container configured to hold a liquid culture medium in communication with the liquid introduction port;

a pump connected to the housing container and separately connected by a liquid feeding valve to a branch point on the liquid feeding pipe disposed between the liquid introduction port and the liquid discharge port;

a gas introduction valve connected to the branch point on the liquid feeding pipe and configured to introduce gas into the liquid feeding pipe;

a liquid sensor disposed between the branch point and the liquid discharge port and configured to detect an advancing liquid level of the liquid culture medium in the liquid feeding pipe; and a controller programmed to control the pump, the liquid feeding valve, and the gas introduction valve based on a signal from the liquid sensor, wherein the branch point is disposed on an upstream side of the liquid feeding pipe from the liquid sensor, wherein the controller is further programmed to:

close the liquid feeding valve and cause the pump to pressurize the housing container to feed the liquid culture medium in the housing container from the liquid introduction port through the liquid feeding pipe towards the liquid sensor, when the signal from the liquid sensor indicates the advancing liquid level, stop the pump and open the gas introduction valve to introduce the gas into the liquid feeding pipe which causes the liquid culture medium in the liquid feeding pipe upstream from the branch point to return to the housing container, and close the gas introduction valve, open the liquid feeding valve and cause the pump to feed the liquid culture medium in the liquid feeding pipe downstream from the branch point to the liquid discharge port.

* * * * *